US009515582B2

(12) United States Patent
Nakanishi et al.

(10) Patent No.: US 9,515,582 B2
(45) Date of Patent: Dec. 6, 2016

(54) DRIVING APPARATUS FOR ANALYZING APPARATUS

(71) Applicant: Panasonic Heathcare Co., Ltd., Toon-shi, Ehime (JP)

(72) Inventors: Kenji Nakanishi, Ehime (JP); Yoshiyuki Fujii, Ehime (JP)

(73) Assignee: PANASONIC HEALTHCARE HOLDINGS CO., LTD., Tokyo (JP)

( * ) Notice: Subject to any disclaimer, the term of this patent is extended or adjusted under 35 U.S.C. 154(b) by 0 days.

(21) Appl. No.: 14/459,997

(22) Filed: Aug. 14, 2014

(65) Prior Publication Data

US 2014/0354193 A1 Dec. 4, 2014

Related U.S. Application Data

(62) Division of application No. 12/747,348, filed as application No. PCT/JP2008/003585 on Dec. 4, 2008, now Pat. No. 8,858,881.

(30) Foreign Application Priority Data

Dec. 10, 2007 (JP) ................................ 2007-317799
Dec. 27, 2007 (JP) ................................ 2007-335426
(Continued)

(51) Int. Cl.
*H02P 5/60* (2006.01)
*H02P 25/32* (2006.01)
(Continued)

(52) U.S. Cl.
CPC ............. *H02P 5/60* (2013.01); *B01F 11/0002* (2013.01); *B01F 13/0059* (2013.01);
(Continued)

(58) Field of Classification Search
CPC ................ H02P 25/027; B01F 11/0008; G01N 2035/00524
See application file for complete search history.

(56) References Cited

U.S. PATENT DOCUMENTS 2,636,742 A 4/1953 Redfield
3,778,790 A 12/1973 Prost et al.
(Continued)

FOREIGN PATENT DOCUMENTS

EP 1 302 244 A1 4/2003
EP 1 437 402 A1 7/2004
(Continued)

OTHER PUBLICATIONS

PTO-892 form, Office Action issued in co-pending U.S. Appl. No. 14/459,994, May 11, 2015.
(Continued)

*Primary Examiner* — Kathryn Wright
(74) *Attorney, Agent, or Firm* — Hamre, Schumann, Mueller & Larson, P.C.

(57) ABSTRACT

Disclosed is an analyzing apparatus including a first drive part (71) for rotating a turntable (101) on which an analyzing device is set, a second drive part (72) selectively engaged with the first drive part (71) to reciprocate the analyzing device, and a third drive part (73) for relatively moving the first drive part (71) and the second drive part (72) a position where the first and second drive parts are engaged with each other and a position where the first and second drive parts are not engaged with each other. Thus in the mixing and agitation of a small amount of fluid, necessary acceleration can be obtained even in a short time.

4 Claims, 40 Drawing Sheets

(30) Foreign Application Priority Data

Jan. 10, 2008 (JP) ................................ 2008-002678
Sep. 22, 2008 (JP) ................................ 2008-241911

(51) Int. Cl.

| | | |
|---|---|---|
| *G01N 35/02* | (2006.01) | |
| *B01L 3/00* | (2006.01) | |
| *B01F 13/00* | (2006.01) | |
| *B01F 15/02* | (2006.01) | |
| *G01N 35/04* | (2006.01) | |
| *B04B 9/10* | (2006.01) | |
| *G01N 35/00* | (2006.01) | |
| *B01F 11/00* | (2006.01) | |
| *H02P 25/02* | (2016.01) | |

(52) U.S. Cl.
CPC ...... *B01F 15/0233* (2013.01); *B01L 3/50273* (2013.01); *G01N 35/025* (2013.01); *G01N 35/04* (2013.01); *H02K 11/215* (2016.01); *H02P 25/032* (2016.02); *B01F 11/0008* (2013.01); *B01F 11/0014* (2013.01); *B01L 2300/043* (2013.01); *B01L 2300/0803* (2013.01); *B01L 2300/087* (2013.01); *B01L 2400/0409* (2013.01); *B01L 2400/0433* (2013.01); *B04B 9/10* (2013.01); *G01N 2035/00495* (2013.01); *G01N 2035/00524* (2013.01); *G01N 2035/00534* (2013.01); *G01N 2035/0449* (2013.01); *G01N 2035/0486* (2013.01); *H02P 25/027* (2013.01)

(56) References Cited

U.S. PATENT DOCUMENTS

| | | |
|---|---|---|
| 5,199,937 A | 4/1993 | Wada et al. |
| 5,382,218 A | 1/1995 | Uchida |
| 2008/0002178 A1 | 1/2008 | Ogawa et al. |
| 2008/0260585 A1 | 10/2008 | Murakami |

FOREIGN PATENT DOCUMENTS

| | | |
|---|---|---|
| JP | 03-127644 | 5/1991 |
| JP | 07-500910 | 1/1995 |
| JP | 2866404 | 12/1998 |
| JP | 2006-110491 | 4/2006 |
| JP | 2006-145451 | 6/2006 |
| WO | WO 93/08893 | 5/1993 |
| WO | 2007/001084 A1 | 1/2007 |
| WO | 2007/077684 A1 | 7/2007 |

OTHER PUBLICATIONS

Extended European Search Report issued in corresponding European application No. 08859590.5 on Sep. 2, 2015 (9 pages).

FIG. 1
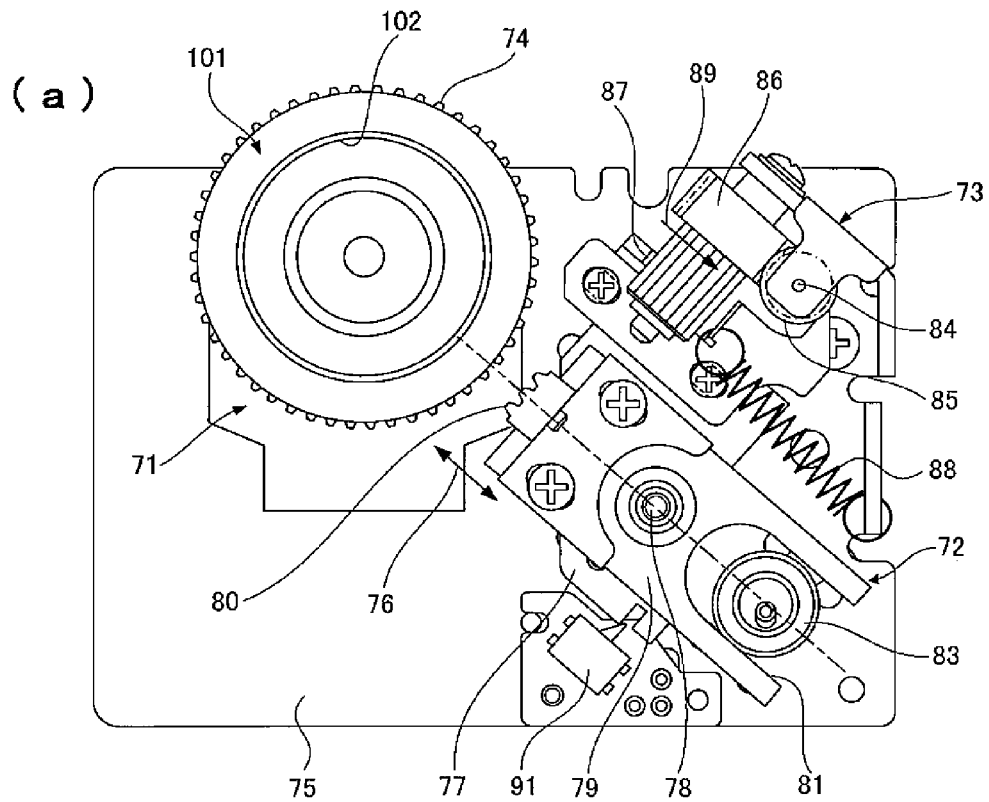
(a)
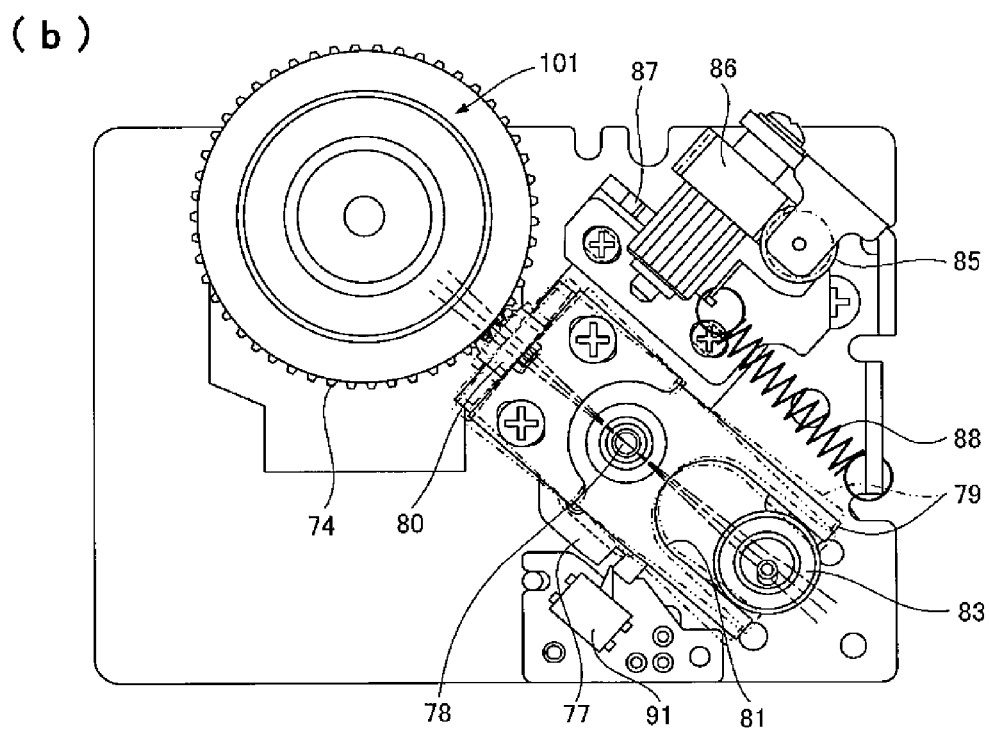
(b)

FIG. 8
(a)
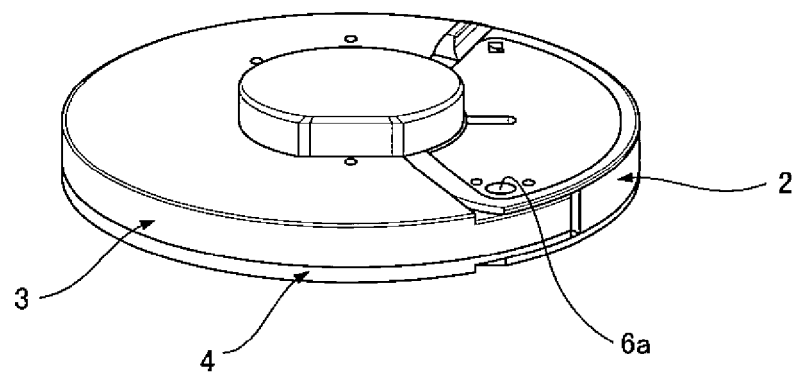
(b)
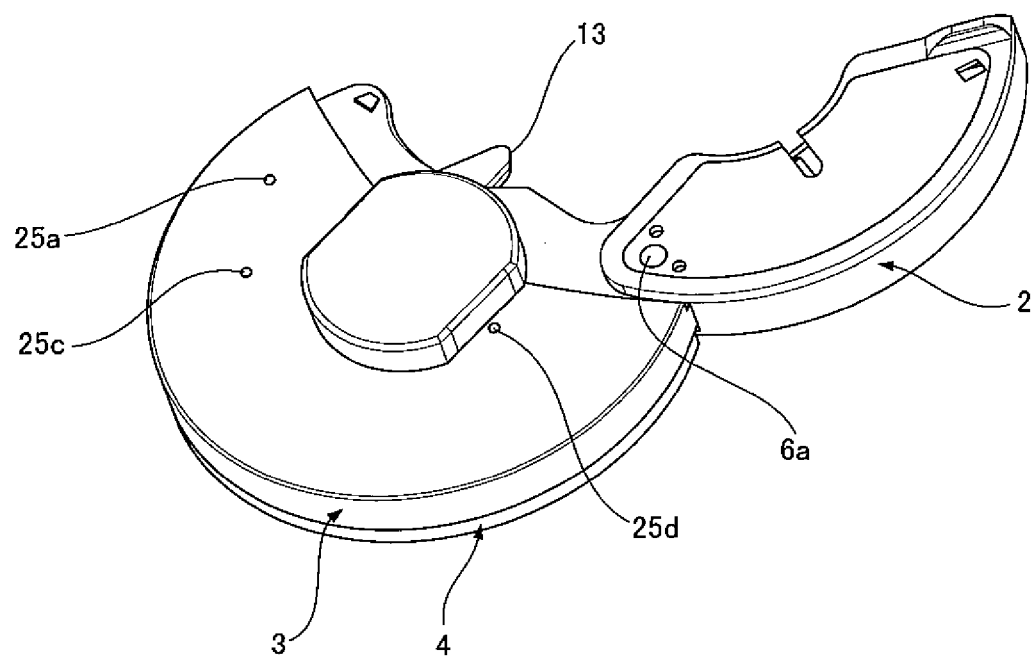

FIG. 11
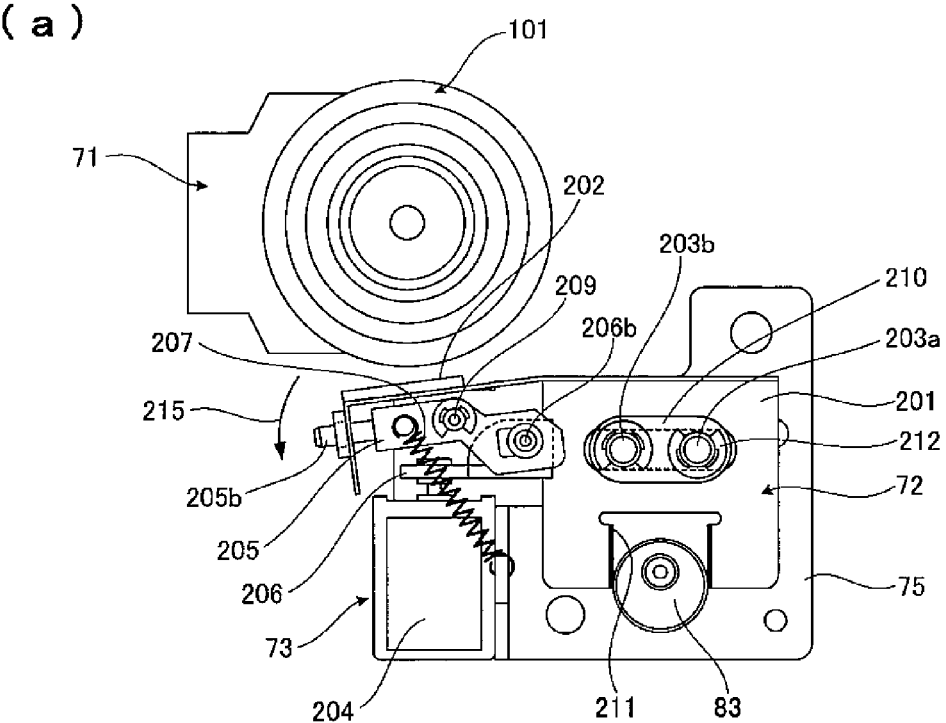
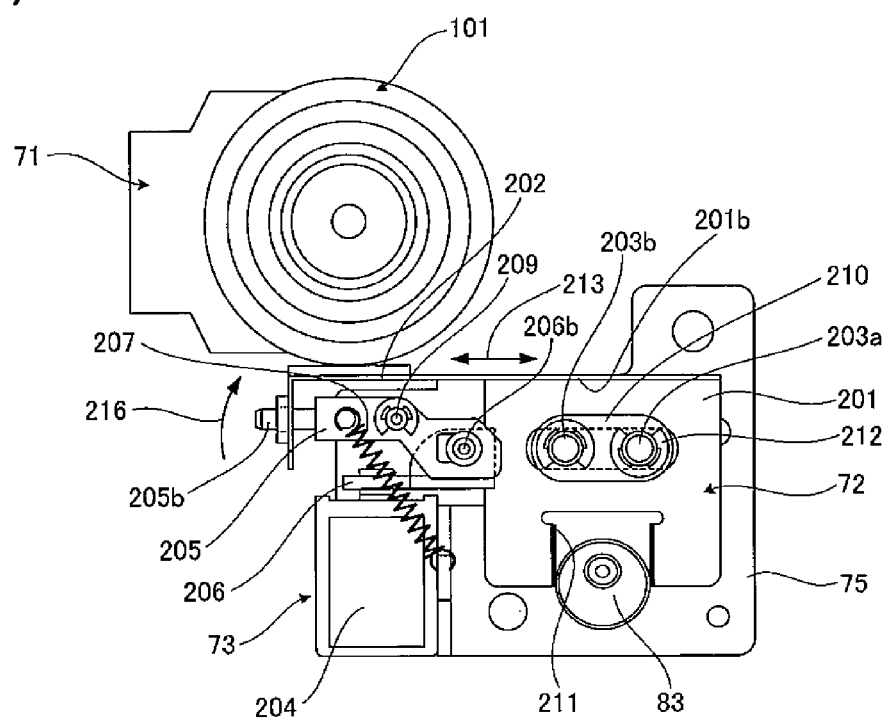

FIG. 40

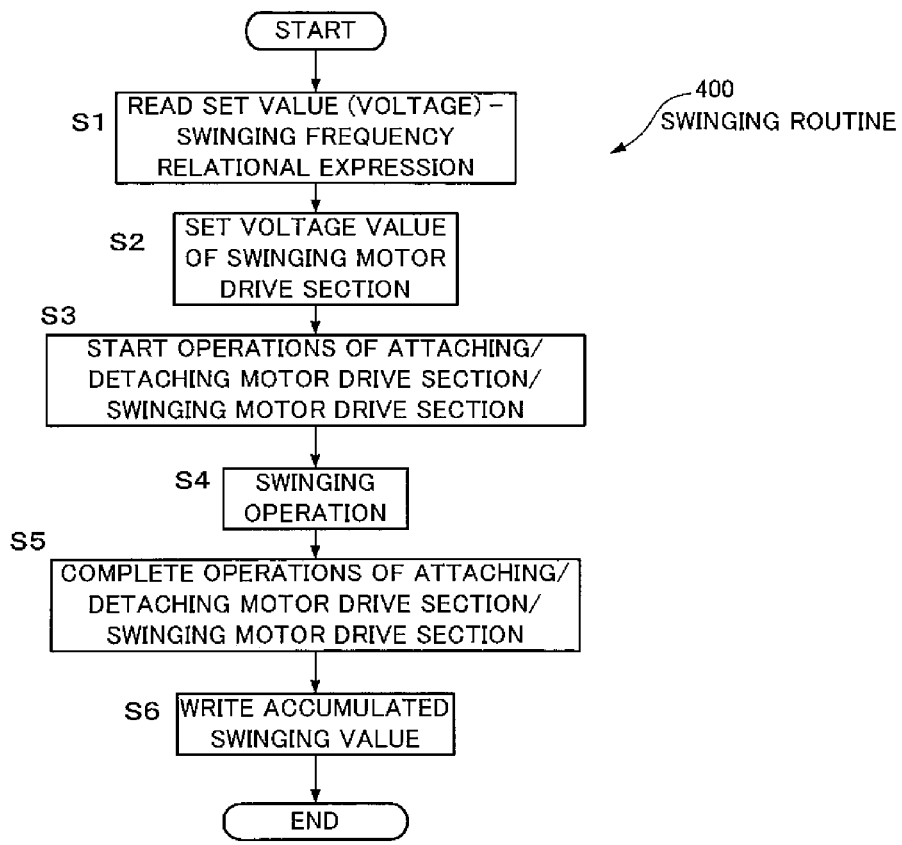

FIG. 41

|  | ADDITIONAL VALUE FOR EACH SWINGING OPERATION |
|---|---|
| SWINGING FREQUENCY 10Hz~20Hz | +1 |
| SWINGING FREQUENCY 21Hz~30Hz | +2 |
| SWINGING FREQUENCY 31Hz~40Hz | +3 |
| ELAPSED TIME FROM SHIPMENT OF PRODUCT (UNTIL FIRST YEAR) | +1 |
| ELAPSED TIME FROM SHIPMENT OF PRODUCT (UNTIL SECOND YEAR) | +1 |
| ELAPSED TIME FROM SHIPMENT OF PRODUCT (UNTIL THIRD YEAR) | +1 |
| ELAPSED TIME FROM SHIPMENT OF PRODUCT (UNTIL FOURTH YEAR) | +2 |
| ELAPSED TIME FROM SHIPMENT OF PRODUCT (UNTIL FIFTH YEAR) | +3 |

| | PREVIOUS TABLE | AFTER CHANGED | |
|---|---|---|---|
| yn | xn(Hz) | xn+1 (Hz) | ∠fn(Hz) |
| 1 | 40 | 12.8 | 15.0 | 2.20 |
| 2 | 60 | 18.9 | 23.0 | 4.10 |
| 3 | 80 | 25.1 | 30.0 | 4.90 |
| 4 | 100 | 31.3 | 35.4 | 4.10 |
| 5 | 120 | 37.4 | 39.0 | 1.60 |

| | a | b |
|---|---|---|
| LINE1 | 2.5 | 2.5 |
| LINE2 | 2.9 | -5.7 |
| LINE3 | 3.7 | -31.1 |
| LINE4 | 5.6 | -96.7 |

$y = a \cdot x + b$
$a = (y1 - y2) / (x1 - x2)$
$b = (x1 \cdot y2 - x2 \cdot y1) / (x1 - x2)$

DRIVING APPARATUS FOR ANALYZING APPARATUS

TECHNICAL FIELD

The present invention relates to an analyzing apparatus for transferring an analyzing device, which contains a sample liquid collected from an organism and the like, to a measuring chamber by a centrifugal force and analyzing the sample liquid.

BACKGROUND ART

In the prior art, a liquid collected from an organism and the like is analyzed by a known analyzing method using an analyzing device having fluid channels formed therein. The analyzing device can control a fluid by using a rotator. By using a centrifugal force, the analyzing device can dilute a sample liquid, measure a solution, separate a solid component, transfer and distribute a separated fluid, and mix a solution and a reagent, thereby enabling various biochemical analyses.

Patent Document 1 describes an analyzing device 50 for transferring a solution by a centrifugal force. As shown in FIG. 49, the analyzing device 50 is configured such that a sample liquid as a specimen is injected into a measuring chamber 52 from an inlet 51 by an inserting instrument such as a pipette, the sample liquid is retained by the capillary force of the measuring chamber 52, and then the sample liquid is transferred to a separating chamber 53 by a rotation of the analyzing device. Such an analyzing device using a centrifugal force as a power source for transferring a liquid is preferably shaped like a disk, so that microchannels for controlling the transfer of liquid can be radially arranged without causing any excessive area.

The sample liquid and a diluent are mixed and agitated by accelerating or decelerating a turntable, on which the analyzing device 50 is set, in the same rotation direction, or rotating the turntable in forward and reverse directions.

Further, in order to analyze a component contained in a sample liquid such as blood and urine, operations such as mixing with a reagent and centrifugal separation are performed in the process. Generally, these operations are performed using an agitator and a centrifugal separator. In an analysis conducted through multiple processes, these operations performed in the respective devices cause low efficiency. To address this problem, a single device for performing centrifugal separation and agitation is proposed in Patent Document 2 and so on.

Unlike in Patent Document 1, Patent Document 2 does not describe an analyzing device but describes a technique of a centrifugal separator of FIG. 50 in which an eccentric cam 803 rotationally driven by a motor 802 is inserted into a hole 801 bored on a substrate 800, so that the substrate 800 is vibrated. Centrifugal separation and agitation are switched by an electromagnetic plunger.

Patent Document 1: National Publication of International Patent Application No. 7-500910
Patent Document 2: Japanese Patent No. 2866404

DISCLOSURE OF THE INVENTION

Problems to be Solved by the Invention

In the configuration of Patent Document 1, however, a sufficient acceleration for performing mixing and agitation in a short time cannot be obtained because of the inertial force of the analyzing device, the response of the drive unit, and so on, so that it takes a long time to perform mixing and agitation under present circumstances.

This disadvantage is apparent particularly in the mixing of a small amount of fluid. Mixing and agitation may be insufficiently performed even in a sufficient period of time.

The present invention has been devised to solve the problem of the prior art. An object of the present invention is to provide an analyzing apparatus that can obtain a necessary acceleration in the mixing and agitation of a small amount of fluid even in a shorter time than in the prior art.

In the configuration of Patent Document 2, centrifugal separation and agitation are performed by different motors. However, it is necessary to keep constant the rotations of the motors to accurately perform the operations. The addition of an agitating function requires another sensor for detecting a frequency, so that the configuration of the apparatus is increased in size and the control is complicated.

The present invention has been devised to solve the problem of the prior art. An object of the present invention is to provide a centrifugal separator using a sensor for controlling centrifugal separation and agitation.

Another object of the present invention is to provide an analyzing apparatus including a rotary drive section that can stably perform swinging even in the event of deformation such as wearing of a component.

Means for Solving the Problems

An analyzing apparatus of the present invention in which an analyzing device is set, the analyzing device having a microchannel structure for transferring a sample liquid to a measuring chamber by a centrifugal force, the analyzing apparatus including: a first drive part for rotating the set analyzing device; a second drive part selectively engaged with the first drive part to reciprocate the analyzing device, and a third drive part for relatively moving the first drive part and the second drive part to a position where the first and second drive parts are engaged with each other and a position where the first and second drive parts are not engaged with each other.

The first drive part is made up of a turntable on which the analyzing device is set, and a first motor for rotationally driving the turntable; and the second drive part is made up of a lever supported so as to reciprocate or swing in the tangential direction of the turntable, and a second motor for driving the lever so as to reciprocate or swing the lever.

An analyzing apparatus of the present invention in which an analyzing device is set, the analyzing device having a microchannel structure for transferring a sample liquid to a measuring chamber by a centrifugal force, the analyzing apparatus including: a first drive part having a turntable on which the analyzing device is set, and a first motor for rotationally driving the turntable; a second drive part having a lever that is supported so as to swing in the tangential direction of the turntable and is selectively engaged with the first drive part, and a second motor for driving the lever in a swinging manner to reciprocate the analyzing device; a third drive part for relatively moving the first drive part and the second drive part to a position where the first and second drive parts are engaged with each other and a position where the first and second drive parts are not engaged with each other; and a control section for controlling the timing of energization to the second motor so as to bring the first drive part and the second drive part close to each other while swinging the lever, when the third drive part relatively moves the first drive part and the second drive part to the position where the first and second drive parts are engaged with each other.

The analyzing apparatus further includes a first gear formed on the outer periphery of the turntable of the first drive part, and a second gear formed on the end of the lever of the second drive part so as to mesh with the first gear.

Further, the first motor is an outer rotor motor, and the first motor includes: a first gear formed on the outer periphery of an outer rotor, and a second gear formed on the end of the lever of the second drive part so as to mesh with the first gear.

Moreover, the control section is set at "f1<f2" where f1 is a first frequency that is the swinging frequency of the lever when the first drive part and the second drive part are relatively moved to the position where the first and second drive parts are engaged with each other, and f2 is a second frequency that is the swinging frequency of the lever after the first drive part and the second drive part are engaged with each other.

Further, in the case where the third drive part relatively moves the first and second drive parts to the position where the first and second drive parts are not engaged with each other, the control section controls a state of energization to the first motor of the first drive part so as to regulate a rotation when the second motor is energized to separate the first drive part and the second drive part.

An analyzing apparatus of the present invention in which an analyzing device is set, the analyzing device having a microchannel structure for transferring a sample liquid to a measuring chamber by a centrifugal force, the analyzing apparatus including: a turntable for holding the analyzing device in which the sample liquid has been injected; a first drive part that rotationally drives the turntable and uses at least two magnetic sensors to detect a rotating magnetic field; a second drive part engaged with the turntable to generate reciprocating vibrations on the turntable; and a vibration detecting section for selecting an output signal having the largest amplitude from the output signals of the magnetic sensors and calculating a vibration frequency from the selected output signal while keeping the selection state until the completion of an operation of vibration agitation.

Moreover, the first drive part has a rotary motor that is a three-phase brushless motor.

The vibration detecting section includes: filters for extracting two of the output signals of the magnetic sensors and removing direct-current signals; a first comparing section for comparing the amplitudes of the output signals of the filters to decide which of the amplitudes is larger, and storing the decision result; a multiplexer for selecting the signal having the largest amplitude from the output signals of the filters based on the decision result stored in the first comparing section; a second comparing section for digitally converting the output signal selected by the multiplexer; and a microcomputer for calculating a vibration frequency from the output signal of the second comparing section.

The vibration detecting section includes: filters for removing direct-current signals from the output signals of the at least two magnetic sensors; a multiplexer for selecting one of the output signals of the filters; an analog-to-digital converter for digitally converting the output signal of the multiplexer; and a microcomputer for calculating a vibration frequency from the output signal of the analog-to-digital converter.

An analyzing apparatus of the present invention including a rotational drive section having a first drive part for rotating a set analyzing device, a second drive part selectively engaged with the first drive part to reciprocate the analyzing device, and a third drive part for relatively moving the first drive part and the second drive part to a position where the first and second drive parts are engaged with each other and a position where the first and second drive parts are not engaged with each other, the analyzing apparatus further including: memory for storing the swinging frequency of the second drive part according to a set value; and a controller for running a swinging routine in which a set value necessary for swinging the analyzing device is read at a desired frequency and is supplied to the second drive part, the controller further running a load fluctuation learning routine in which a set value for learning is supplied to the second drive part to measure the swinging frequency and the contents of the memory are updated so as to reduce fluctuations in swinging frequency according to the measured value.

Further, the controller runs an accumulated swinging value deciding routine in which count values corresponding to the contents of a swinging operation are accumulated in the swinging routine, the load fluctuation learning routine is instructed to run when the controller detects that the accumulated value has exceeded a threshold value, and then the accumulated value is reset.

Moreover, the controller runs an accumulated swinging value deciding routine in which count values corresponding to the contents of a swinging operation and count values corresponding to secular changes are accumulated in the swinging routine, the load fluctuation learning routine is instructed to run when the controller detects that the accumulated value has exceeded a threshold value, and then the accumulated value is reset.

Further, the controller supplies a single set value for learning to the second drive part and measures the swinging frequency in the load fluctuation learning routine, and the controller updates the contents of the memory so as to reduce fluctuations in swinging frequency according to the measured value.

Moreover, the controller supplies multiple set values for learning to the second drive part and measures the swinging frequencies in the load fluctuation learning routine, and the controller updates the contents of the memory so as to reduce fluctuations in swinging frequency by linear approximation between the two points of the measured values.

Advantage of the Invention

With this configuration, an analyzing device set on a first drive part is reciprocated by engaging a second drive part with the first drive part. Thus it is possible to obtain necessary acceleration even in a short time unlike in the prior art where a sample liquid and a diluent are mixed and agitated by accelerating or decelerating the motor of a first drive part in the same rotation direction, or rotating the motor in forward and reverse directions.

The control section controls the timing of energization to the second motor so as to bring the first drive part and the second drive part close to each other while swinging the lever. Thus it is possible to reduce an impact and achieve stable engagement when the first drive part and the second drive part are engaged with each other.

Further, it is possible to calculate a vibration frequency in agitation based on the detected output of a magnetic sensor used for a rotary motor for centrifugal separation. Thus it is not necessary to provide a sensor for controlling agitation in addition to the rotary motor for centrifugal separation.

Moreover, even in the event of mechanical fluctuations including load fluctuations in at least one of the first drive part and the second drive part, the controller periodically and automatically corrects a set value for instructing the second drive part. Thus it is possible to reduce fluctuations in the swinging frequency of the analyzing device and keep the analysis accuracy over an extended period.

BRIEF DESCRIPTION OF THE DRAWINGS

FIGS. 1(a) and 1(b) are plan views showing the disengagement of a first drive part and a second drive part of a rotational drive section of an analyzing apparatus and a plan view showing the engagement of the first drive part and the second drive part according to a first embodiment of the present invention;

FIGS. 8(a) and 8(b) are outside perspective views showing the analyzing device with an opened and closed protective cap according to the first embodiment of the present invention;

FIGS. 11(a) and 11(b) are plan views before and after the driving of a rotational drive section according to a second embodiment of the present invention;

FIG. 40 is a flowchart showing a swinging routine according to the seventh embodiment;

FIG. 41 is an explanatory drawing showing an additional value table according to the seventh embodiment;

BEST MODE FOR CARRYING OUT THE INVENTION

First Embodiment

FIGS. 1 to 10 show an analyzing apparatus according to a first embodiment of the present invention.

Figure 9:
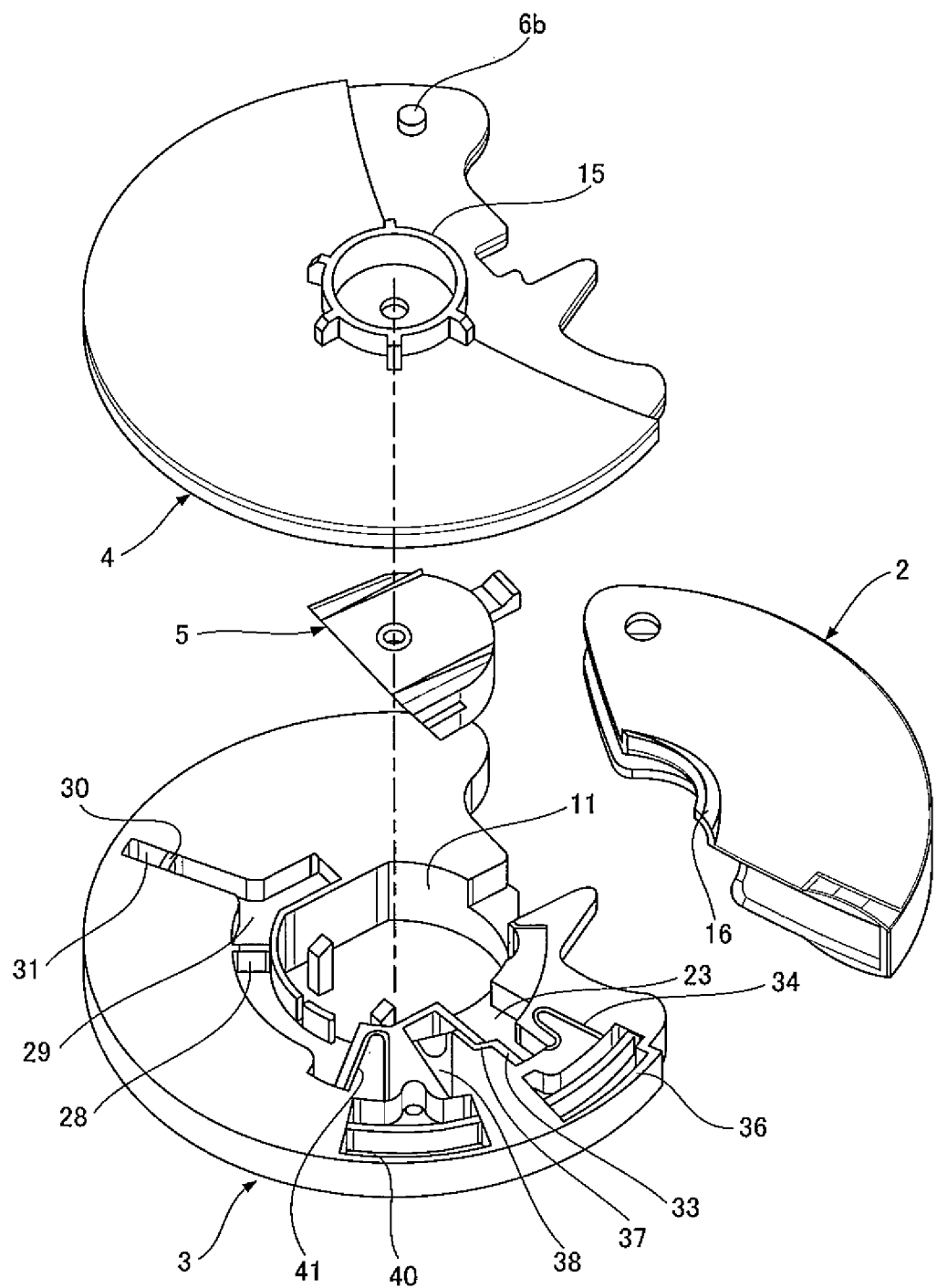
FIG. 9 is an exploded perspective view showing the analyzing device of the first embodiment.
Figure 10:
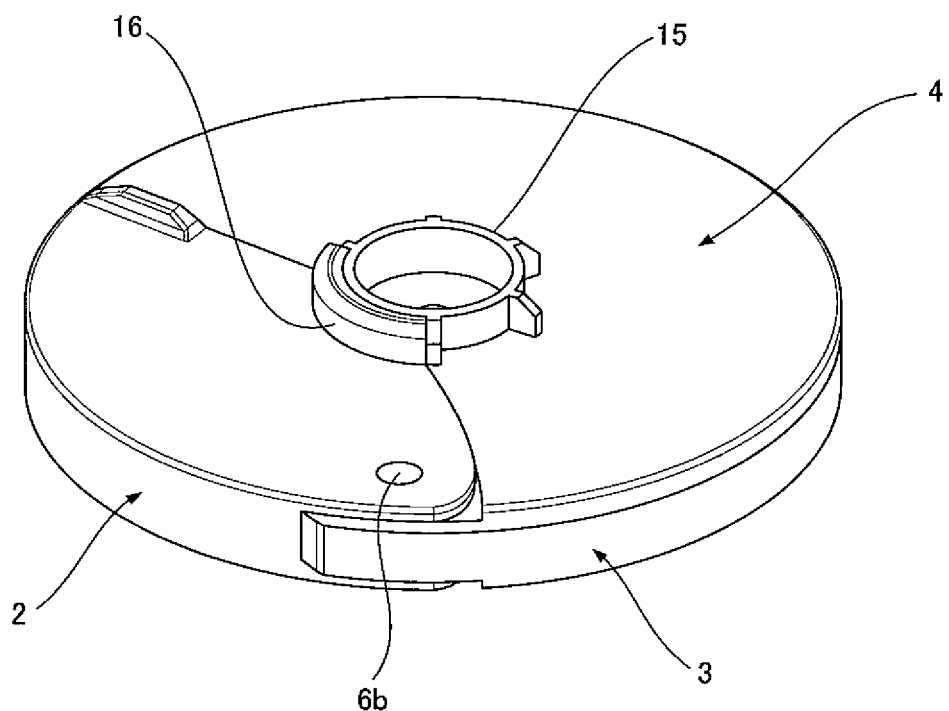
FIG. 10 is a perspective view taken from the back of the analyzing device with the protective cap closed.

FIGS. 8 to 10 show an analyzing device.

FIGS. 8(a) and 8(b) show an analyzing device 1 with an opened and closed protective cap 2. FIG. 9 is an exploded view of the analyzing device 1 with the underside of FIG. 8(a) placed face up. FIG. 10 is an assembly drawing of FIG. 8(b).

The analyzing device shown in FIGS. 8 and 9 is made up of four components of a base substrate 3 having a microchannel structure formed on one surface, the microchannel structure having a minutely uneven surface, a cover substrate 4 for covering the surface of the base substrate 3, a diluent container 5 for retaining a diluent, and the protective cap 2 for preventing splashes of a sample liquid.

The base substrate 3 and the cover substrate 4 are joined to each other with the diluent container 5 and so on set in the base substrate 3 and the cover substrate 4, and the protective cap 2 is attached to the joined base substrate 3 and cover substrate 4.

The cover substrate 4 covers the openings of several recessed portions formed on the top surface of the base substrate 3, thereby forming a plurality of storage areas, the passages of the microchannel structure for connecting the storage areas, and so on. Reference numeral 11 denotes a diluent container storage part, reference numeral 23 denotes a separating cavity, reference numerals 25a, 25b, 25c, and 25d denote air holes, reference numeral 28 denotes an overflow passage, reference numeral 29 denotes an overflow cavity, reference numeral 31 denotes a reference measuring chamber, reference numeral 33 denotes a capillary cavity, reference numeral 34 denotes a connecting passage, reference numeral 36 denotes an overflow cavity, reference numeral 37 denotes a capillary passage, reference numeral 38 denotes a measuring passage, reference numeral 40 denotes a measuring chamber, and reference numeral 41 denotes a connecting passage.

Reagents required for various analyses are stored beforehand in necessary ones of the storage areas. One side of the protective cap 2 is pivotally supported such that the protective cap 2 can be opened and closed in engagement with shafts 6a and 6b formed on the base substrate 3 and the cover substrate 4. When a sample liquid to be inspected is blood, the passages of the microchannel structure in which a capillary force is applied have clearances of 50 μm to 300 μm.

The outline of an analyzing process using the analyzing device 1 is that a sample liquid is dropped into the analyzing device 1 in which the diluent has been set, at least a part of the sample liquid is diluted with the diluent, and then a measurement is conducted.

Figure 5:
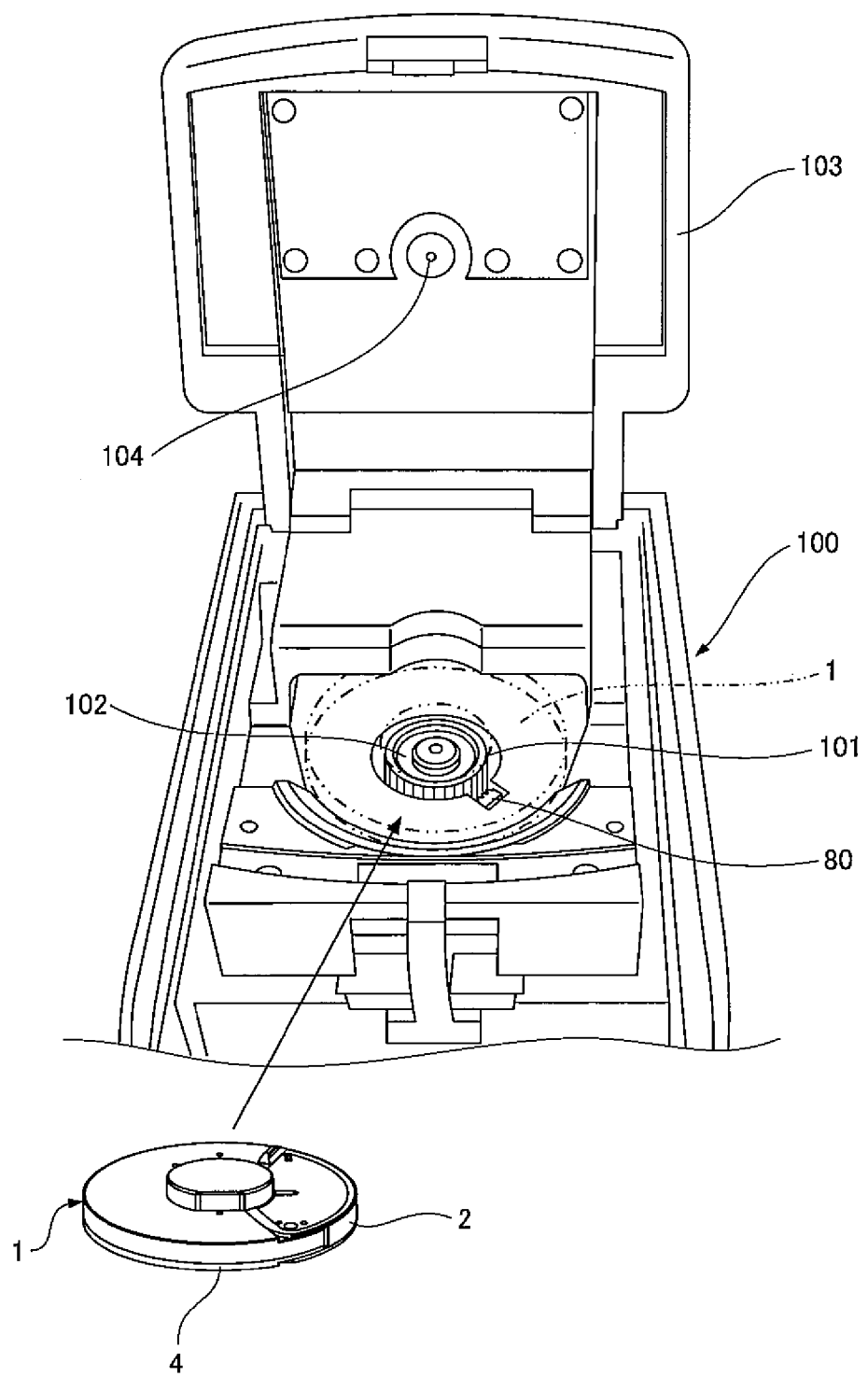
FIG. 5 is a perspective view showing that the door of the analyzing apparatus is opened according to the first embodiment.
Figure 6:
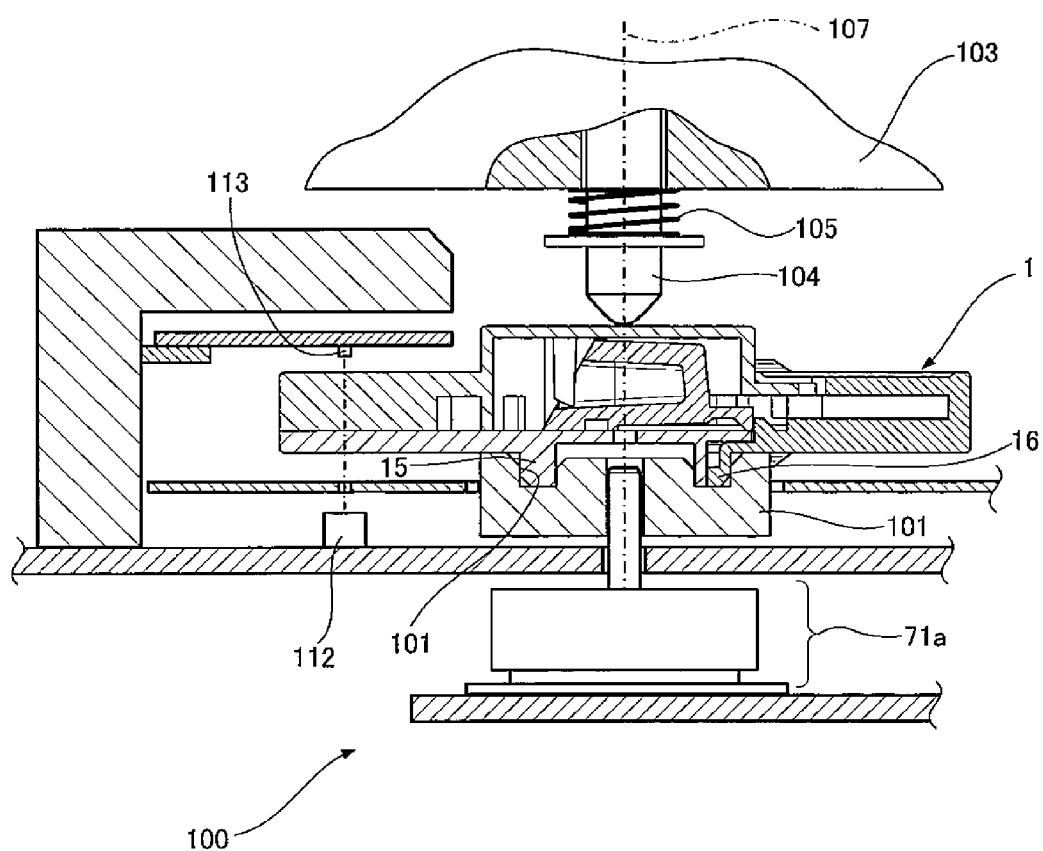
FIG. 6 is a sectional view showing the main part of an analyzing device set in the analyzing apparatus.

The analyzing device 1 is set on a turntable 101 of an analyzing apparatus 100 shown in FIGS. 5 and 6.

On the top surface of the turntable 101, a groove 102 is formed. In a state in which the analyzing device 1 is set on the turntable 101, a rotary support part 15 formed on the cover substrate 4 of the analyzing device 1 and a rotary support part 16 formed on the protective cap 2 are engaged with the groove 102, so that the analyzing device 1 is stored.

After the analyzing device 1 is set on the turntable 101, a door 103 of the analyzing apparatus is closed before a rotation of the turntable 101, so that the set analyzing device 1 is pressed to the side of the turntable 101 by a movable piece 104 provided on the side of the door 103, with a biasing force of a spring 105 at a position on the rotation axis of the turntable 101. Thus the analyzing device 1 rotates together with the turntable 101 that is rotationally driven by a rotational drive section 106. Reference numeral 107 denotes the axis of rotation of the turntable 101.

Figure 7:
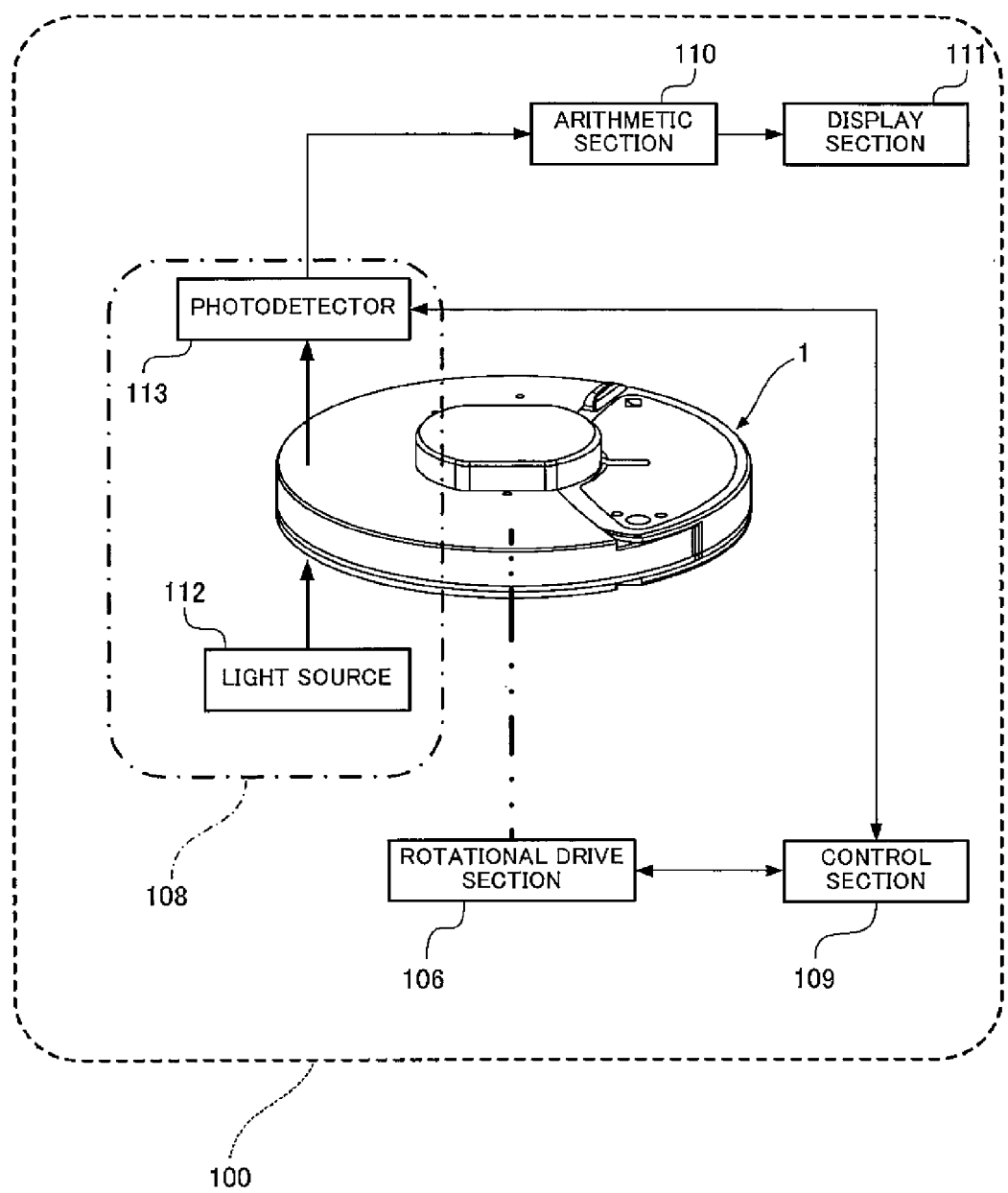
FIG. 7 is a block diagram showing the analyzing apparatus according to the first embodiment.

FIG. 7 shows the overall configuration of the analyzing apparatus 100.

The analyzing apparatus 100 is made up of the rotational drive section 106 for rotating the turntable 101, an optical measurement section 108 for optically measuring a solution in the analyzing device 1, a control section 109 for controlling the rotation speed and direction of the turntable 101, the measurement timing of the optical measurement section, and so on, an arithmetic section 110 for calculating a measurement result by processing a signal obtained by the optical measurement section 108, and a display section 111 for displaying the result obtained by the arithmetic section 110.

The rotational drive section 106 can rotate the analyzing device 1 through the turntable 101 about a rotation axis 107 in any direction at a predetermined rotation speed and can further vibrate the analyzing device 1 so as to laterally reciprocate the analyzing device 1 at a predetermined stop position with respect to the rotation axis 107 with a predetermined amplitude range and a predetermined period.

The optical measurement section 108 includes a light source 112 (may be a light emitting diode) for emitting light of a specific wavelength to the measuring part of the analyzing device 1, and a photodetector 113 for detecting an amount of light having passed through the analyzing device 1 out of the light emitted from the light source 112.

The analyzing device 1 is rotationally driven by the turntable 101, and the sample liquid drawn into the analyzing device 1 from an inlet 13 is transferred in the analyzing device 1 by using a centrifugal force generated by rotating the analyzing device 1 about the rotation axis 107 located inside the inlet 13 and the capillary force of the capillary passage provided in the analyzing device 1.

FIGS. 1 to 4 specifically show the rotational drive section 106 of the analyzing apparatus 100.

A first drive part 71 for rotating the set analyzing device 1 is made up of a first motor 71a of outer rotor type and the turntable 101 that is attached to the output shaft of the first motor 71a and has the analyzing device 1 set thereon. On the outer periphery of the turntable 101, a first gear 74 is formed.

In addition to the first drive part 71, the rotational drive section 106 includes a second drive part 72 that is selectively engaged with the first drive part 71 to laterally reciprocate the turntable 101 at a predetermined stop position with respect to the rotation axis 107 with a predetermined amplitude range and a predetermined period and reciprocates the analyzing device 1, and a third drive part 73 for relatively moving the first and second drive parts 71 and 72 to a position where the first and second drive parts 71 and 72 are engaged with each other (FIG. 1(b)) and a position where the drive parts are not engaged with each other (FIG. 1(a)). In the present embodiment, the second drive part 72 moves relative to the first drive part 71.

Figure 2:
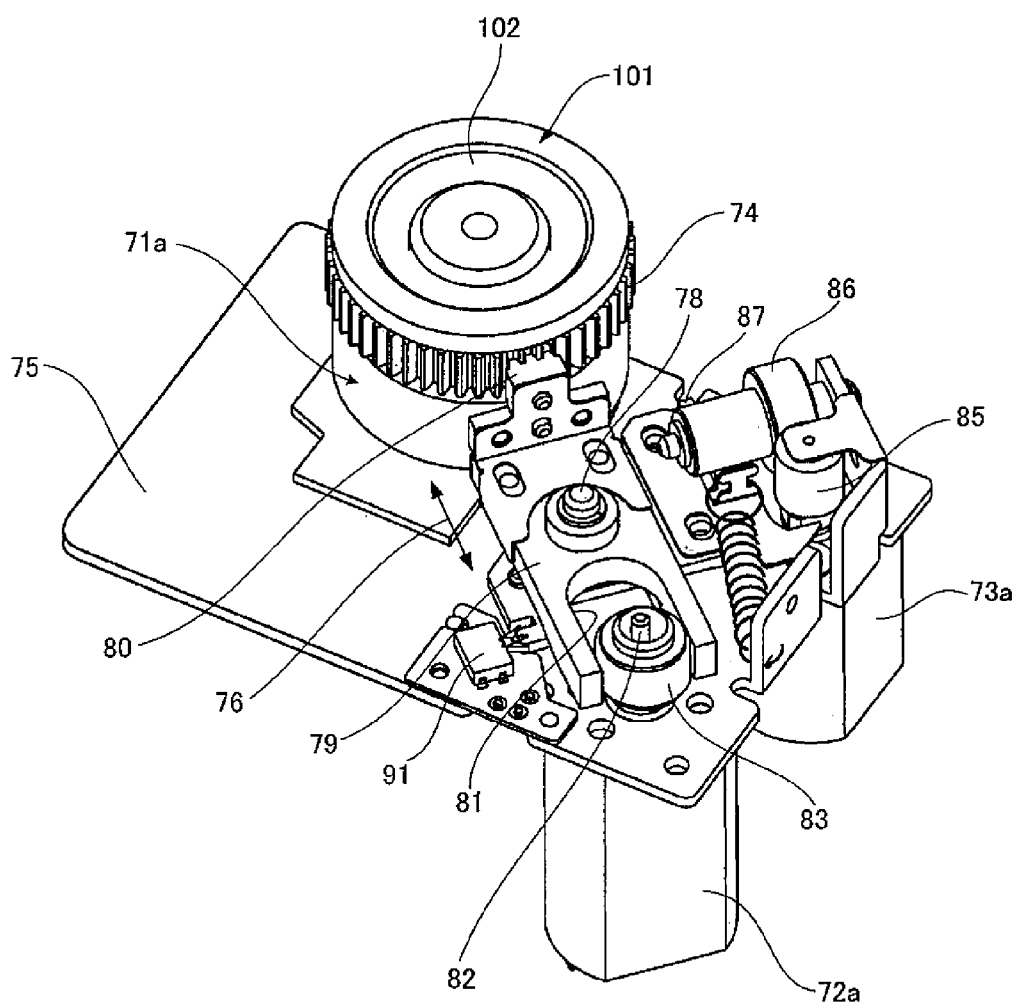
FIG. 2 is a perspective view showing a rotational drive section of the first embodiment.
Figure 3:
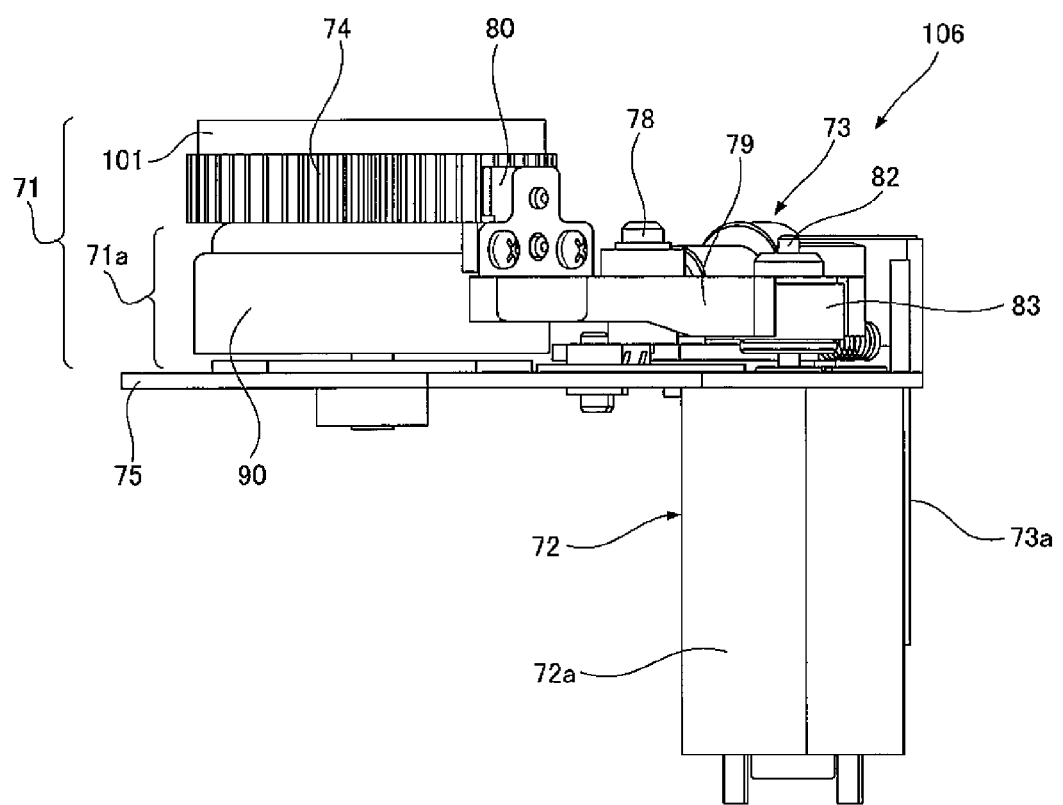
FIG. 3 is a side view showing the rotational drive section of the first embodiment.
Figure 4:
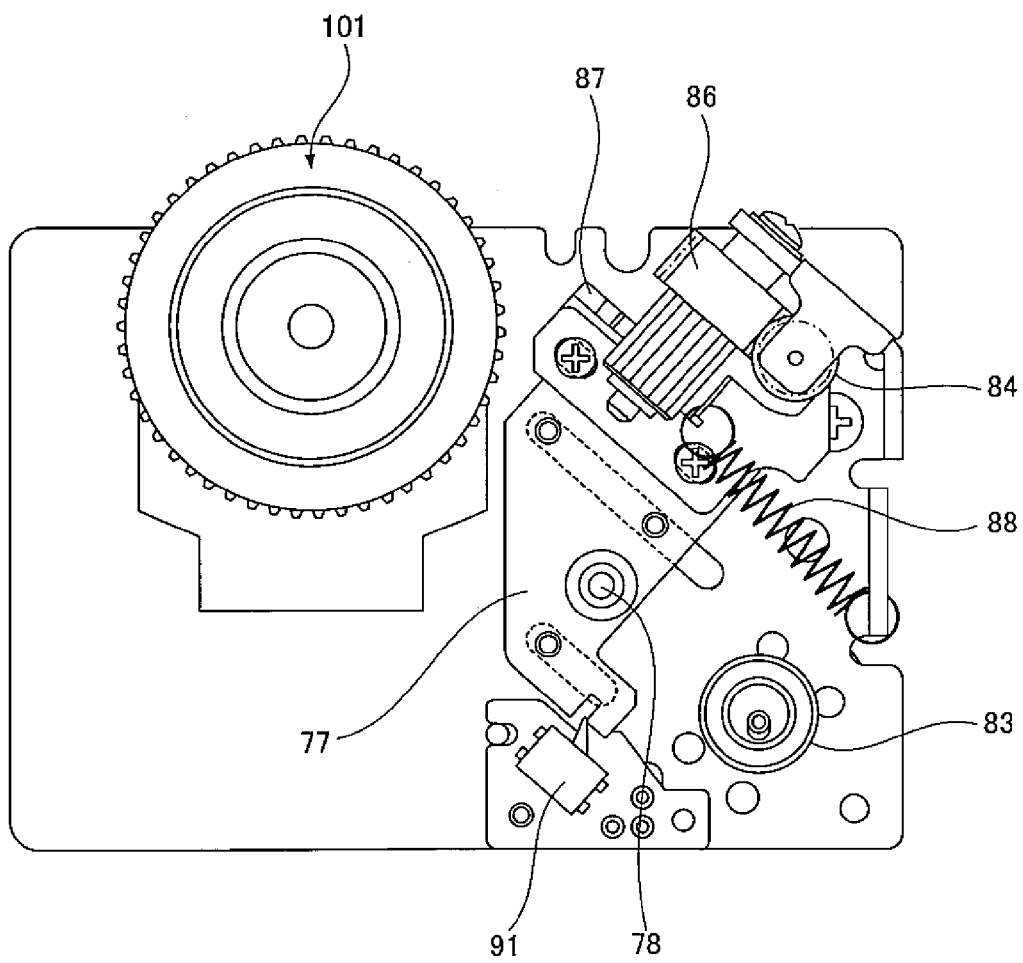
FIG. 4 is a plan view showing that a lever of the second drive part has been removed according to the first embodiment.

The second drive part 72 and the third drive part 73 are configured as shown in FIGS. 2 to 4.

On a chassis 75 where the first motor 71a is attached, a second motor 72a, a third motor 73a, and so on are attached. On a support table 77 attached to the chassis 75 so as to slide along an arrow 76 (see FIGS. 1(a) and 2), a support shaft 78 is mounted.

Further, a lever 79 is pivoted on the support shaft 78. On one end of the lever 79 on the side of the turntable 101, a second gear 80 is formed so as to mesh with the first gear 74 of the turntable 101. On the other end of the lever 79, a recessed portion 81 is formed. On the recessed portion 81, an eccentric cam 83 is engaged that is attached to an output shaft 82 of the second motor 72a. FIG. 4 is a plan view showing that the lever 79 has been removed from the support shaft 78.

With this configuration, when the second motor 72a is energized, the lever 79 swings between a solid line position and a virtual line position via the eccentric cam 83.

The lever 79 is urged by a helical spring (not shown) to reduce the backlash of the lever 79 during swinging.

The third drive part 73 is made up of the third motor 73a attached to the chassis 75, a worm 85 attached to an output shaft 84 of the third motor 73a, a worm wheel 86 that is rotationally attached to the chassis 75 and meshes with the worm 85, and a rack 87 that is formed on the support table 77 and meshes with the worm wheel 86. Between the support table 77 and the chassis 75, an extension spring 88 is interposed to reduce backlash between the worm wheel 86 and the rack 87.

With this configuration, the third motor 73a is energized to rotate the worm wheel 86 along an arrow 89 (see FIG. 1(a)) until a detection switch 91 detects the support table 77 as shown in FIG. 1(b), so that the support table 77 on which the rack 87 meshes with the worm wheel 86 slides close to the turntable 101 and the second gear 80 of the lever 79 meshes with the first gear 74 of the turntable 101 as shown in FIG. 1(b). In this state, the second motor 72a kept energized enables the lever 79 to swingingly drive the turntable 101 in the tangential direction of the turntable 101. Thus by increasing the number of revolutions of the second motor 72a, acceleration high enough to agitate a small amount of fluid in the analyzing device 1 can be obtained even in a short time.

In the present embodiment, the lever 79 of the second drive part 72 is brought close to the turntable 101. In the agitation and swinging of the analyzing device 1, the turntable 101 may be brought close to the lever 79 of the second drive part 72 to allow the first and second gears 74 and 80 to mesh with each other. Alternatively, in the agitation and swinging of the analyzing device 1, the turntable 101 of the first drive part 71 and the lever 79 of the second drive part 72 may be brought close to each other to allow the first and second gears 74 and 80 to mesh with each other. Thus the analyzing device 1 can be agitated and swung by relatively moving the first drive part 71 and the second drive part 72 by the third drive part 73 to a position where the lever 79 and the turntable 101 are engaged with each other and a position where the lever 79 and the turntable 101 are not engaged with each other.

In the foregoing embodiments, the analyzing device 1 is agitated and swung by engagement of the first gear 74 of the turntable 101 and the second gear 80 of the lever 79. Instead of the second gear 80 on the lever 79, a friction member provided on one end of the lever 79 may be brought into contact with the first gear 74 of the turntable 101 to engage the turntable 101 and the lever 79.

In the foregoing embodiments, the second drive part 72 is driven in engagement with the first gear 74 provided on the turntable 101. The first gear 74 may be formed on the outer periphery of an outer rotor 90 of the first motor 71a and the second gear 80 of the second drive part 72 may mesh with the first gear 74. Alternatively, the second drive part 72 to be swingingly driven may come into contact with the outer periphery of the outer rotor 90 of the first motor 71a to laterally reciprocate the analyzing device 1 with respect to the rotation axis 107 with the predetermined amplitude range and the predetermined period.

Second Embodiment

Figure 12:
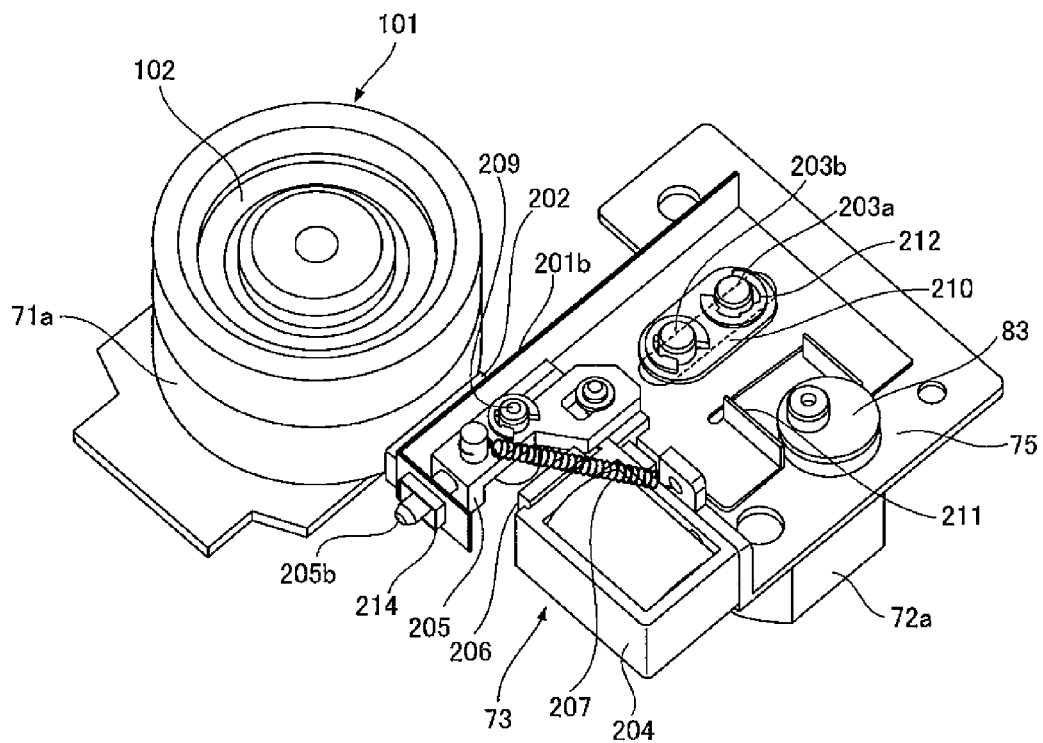
FIG. 12 is a perspective view showing a rotational drive section of the second embodiment.

FIGS. 11 and 12 show a second embodiment of the present invention.

In the rotational drive section 106 of the first embodiment, the analyzing device is reciprocated by swingingly driving the second drive part in the tangential direction of the turntable. The second embodiment of FIGS. 11 and 12 is different in that a second drive part is reciprocated in the tangential direction of a turntable. Another different point is that the driving source of a third drive part is a solenoid.

Regarding the different points from the first embodiment, the operations will be specifically described below.

As shown in FIGS. 11 and 12, a second motor 72a, a solenoid 204, support shafts 203a and 203b, a support shaft 209, and the like are attached to a chassis 75 where a first motor 71a has been attached.

On the support shafts 203a and 203b, a lever 201 is slidably pivoted by a spacer 210 and fasteners 212. On the side of the turntable 101a, the lever 201 has a side bent in parallel with the rotor of the first motor 71a. Further, a friction member 202 that can be in friction contact with the rotor of the first motor 71a is mounted on the end of a bent side 201b. The friction member 202 is made of a material such as cork and butyl rubber. Further, a recessed portion 211 is formed on the lever 201 and an eccentric cam 83 attached to an output shaft 82 of the second motor 72a is engaged with the recessed portion 211.

With this configuration, when the second motor 72a is energized, the lever 201 reciprocates via the eccentric cam 83 as indicated by an arrow 213 of FIG. 11.

A third drive part 73 is made up of a solenoid 204 attached to the chassis 75, a lever 206 engaged with the solenoid 204, and a lever 205 that has an intermediate portion pivoted on the support shaft 209 implanted on the chassis 75 and has one end engaged with a shaft 206b implanted on the lever 206. Further, an other end 205b of the lever 205 is inserted into a hole 214 of the lever 201 and is engaged with the end of the bent side 201b.

The lever 205 urges the end of the bent side 201b of the lever 201 along an arrow 215 of FIG. 11(a) by an extension spring 207. The bent side 201b acts as a plate spring.

With this configuration, the energized solenoid 204 moves the lever 206 and simultaneously rotates the lever 205 along an arrow 216 of FIG. 11(b) with the support shaft 209 serving as a rotation axis. A plate spring portion recovers on the end of the bent side 201b of the lever 201, and the friction member 202 comes into contact with the rotor of the first motor 71a.

In this state, the second motor 72a kept energized enables the lever 79 to swingingly drive a turntable 101 in the tangential direction of the turntable 101. Thus by increasing the number of revolutions of the second motor 72a, acceleration high enough to agitate a small amount of fluid in the analyzing device 1 can be obtained even in a short time.

In the present embodiment, the lever 201 of the second drive part 72 is brought close to the first motor 71a. In the agitation and swinging of an analyzing device 1, the first motor 71a may be brought close to the lever 201 of the second drive part 72. Alternatively, in the agitation and swinging of the analyzing device 1, the first drive part 71 and the lever 201 of the second drive part 72 may be brought close to each other. The analyzing device 1 can be agitated and swung by relatively moving the first drive part 71 and the second drive part 72 by the third drive part 73 to a position where the lever 201 and the first motor 71a are engaged with each other and a position where the lever 201 and the first motor 71a are not engaged with each other.

Although the friction member 202 is engaged with the first motor 71a, the friction member 202 of the lever 201 may be replaced with a gear member as in the first embodiment and the gear member may be engaged with the turntable 101 or a first gear 74 provided on the first motor 71a.

Third Embodiment

The control section 109 of the first, second, and third motors 71a, 72a, and 73a of the first embodiment is configured as will be described below. Thus even when the tops of the teeth of a second gear 80 and the tops of the teeth of a first gear 74 collide each other, the tops of the teeth of the second gear 80 can be reliably engaged with the bottoms of the teeth of the first gear 74, achieving stable mixing and agitation for an analyzing device 1.

Figure 13:
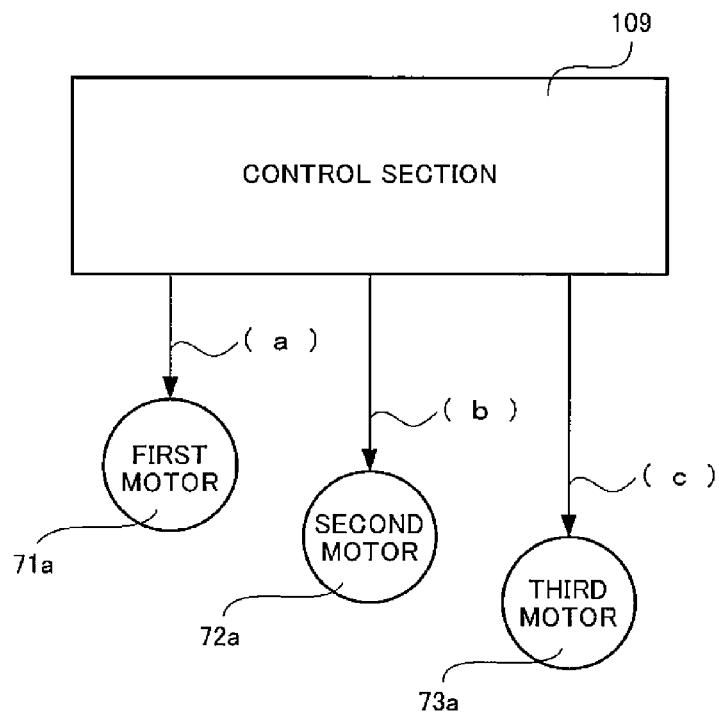
FIG. 13 is a connection diagram showing a control section and first to third motors according to the second embodiment.
Figure 14:
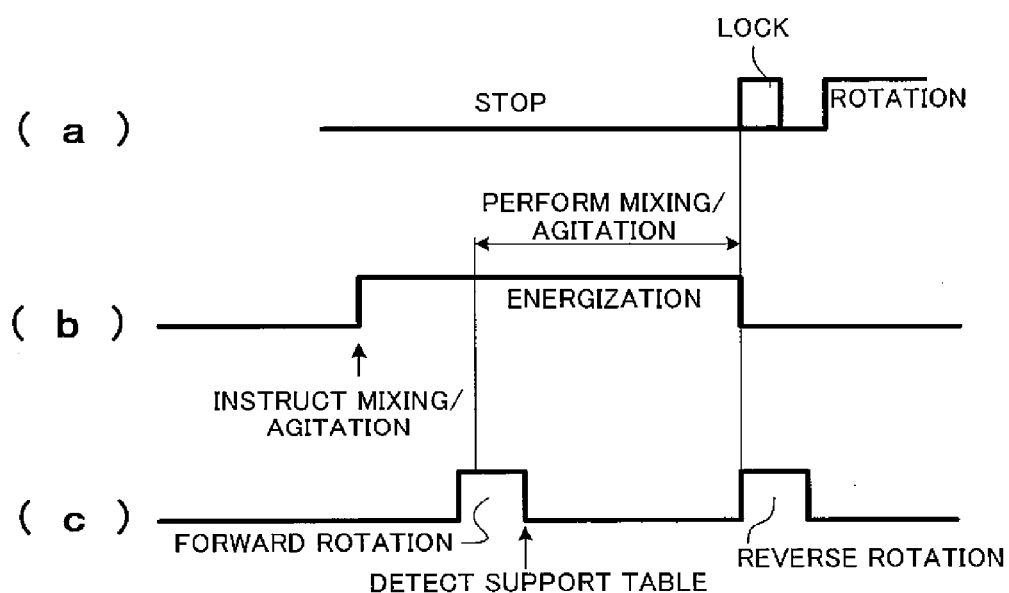
FIGS. 14(a)-(c) are waveform diagrams showing the output signals of the control section according to the second embodiment.

In the case where signals are outputted from the control section 109 to the first motor 71a, the second motor 72a, and the third motor 73a during mixing and agitation as indicated by (a), (b), and (c) in FIG. 13, the control section 109 is configured as shown in FIG. 14.

To be specific, when the control section 109 detects an instruction of agitation/mixing during the stop period of the first motor 71a, the control section 109 starts energizing the second motor 72a before energizing the third motor 73a to make a forward rotation. Thus a lever 79 is swung between a solid line position and a virtual line position by an eccentric cam 83.

After the start of energization to the second motor 72a, the control section 109 energizes the third motor 73a to make a forward rotation. Thus a support table 77 comes close to a turntable 101. The energization to the third motor 73a is completed when a detection switch 91 detects the support table 77 as shown in FIG. 1(b).

When the support table 77 comes close to the turntable 101 thus, the second gear 80 on the end of the lever 79 comes close to the first gear 74 of the turntable 101 while swinging in the tangential direction of the turntable 101. Thus even when the tops of the teeth of the second gear 80 and the tops of the teeth of the first gear 74 collide with each other, the swinging of the second gear 80 reliably engage the tops of the teeth of the second gear 80 with the bottoms of the teeth of the first gear 74, achieving stable mixing and agitation for the analyzing device 1.

The number of revolutions of the second motor 72a is set lower when the first gear 74 and the second gear 80 are moved to an engagement position than after the first gear 74 and the second gear 80 are engaged with each other, and the relationship of "f1<f2" is set where f1 is a first frequency that is the swinging frequency of the lever 79 when the first gear 74 and the second gear 80 are moved to the engagement position, and f2 is a second frequency that is the swinging frequency of the lever 79 after the first gear 74 and the second gear 80 are engaged with each other.

The second gear 80 is separated from the first gear 74 as shown in FIG. 1(a) from the state of FIG. 1(b). This operation is performed in a state in which the control section 109 regulates the rotations of the rotor of the first motor 71a as shown in FIGS. 14 to 16.

Figure 15:
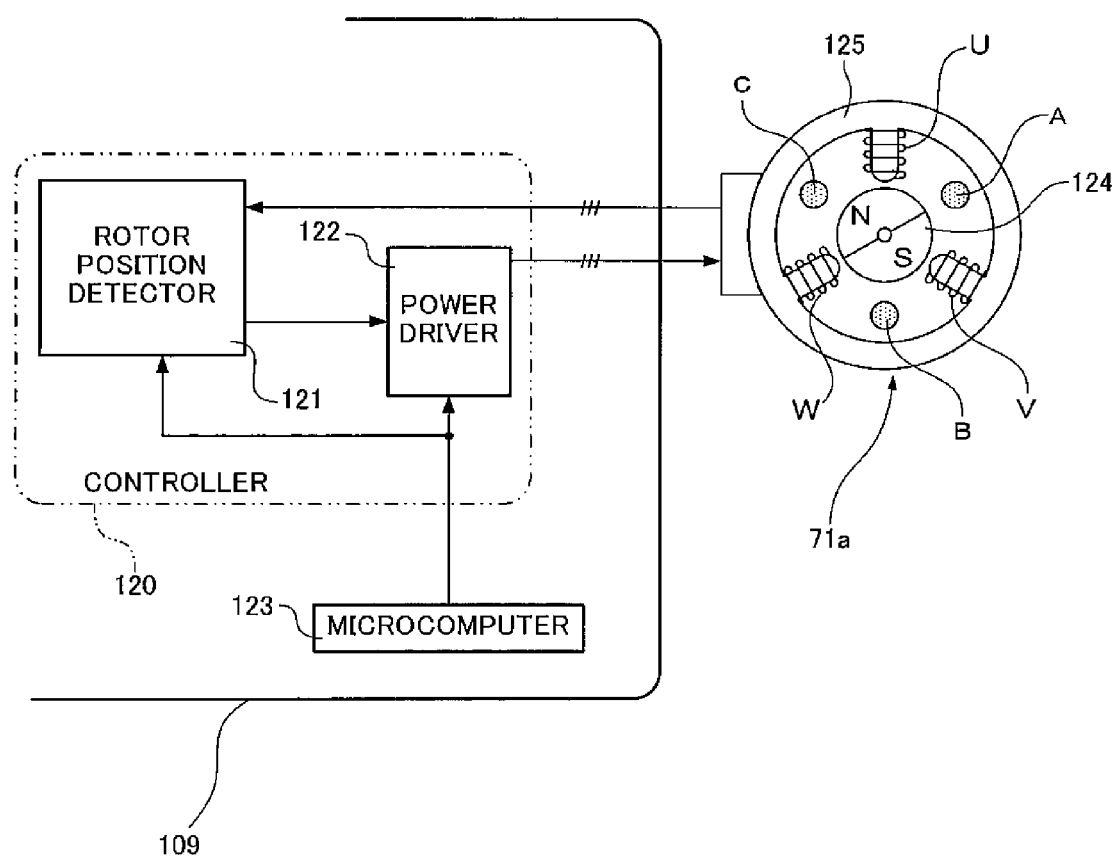
FIG. 15 is a detailed connection diagram of the control section and the first motor according to the second embodiment.
Figure 16:
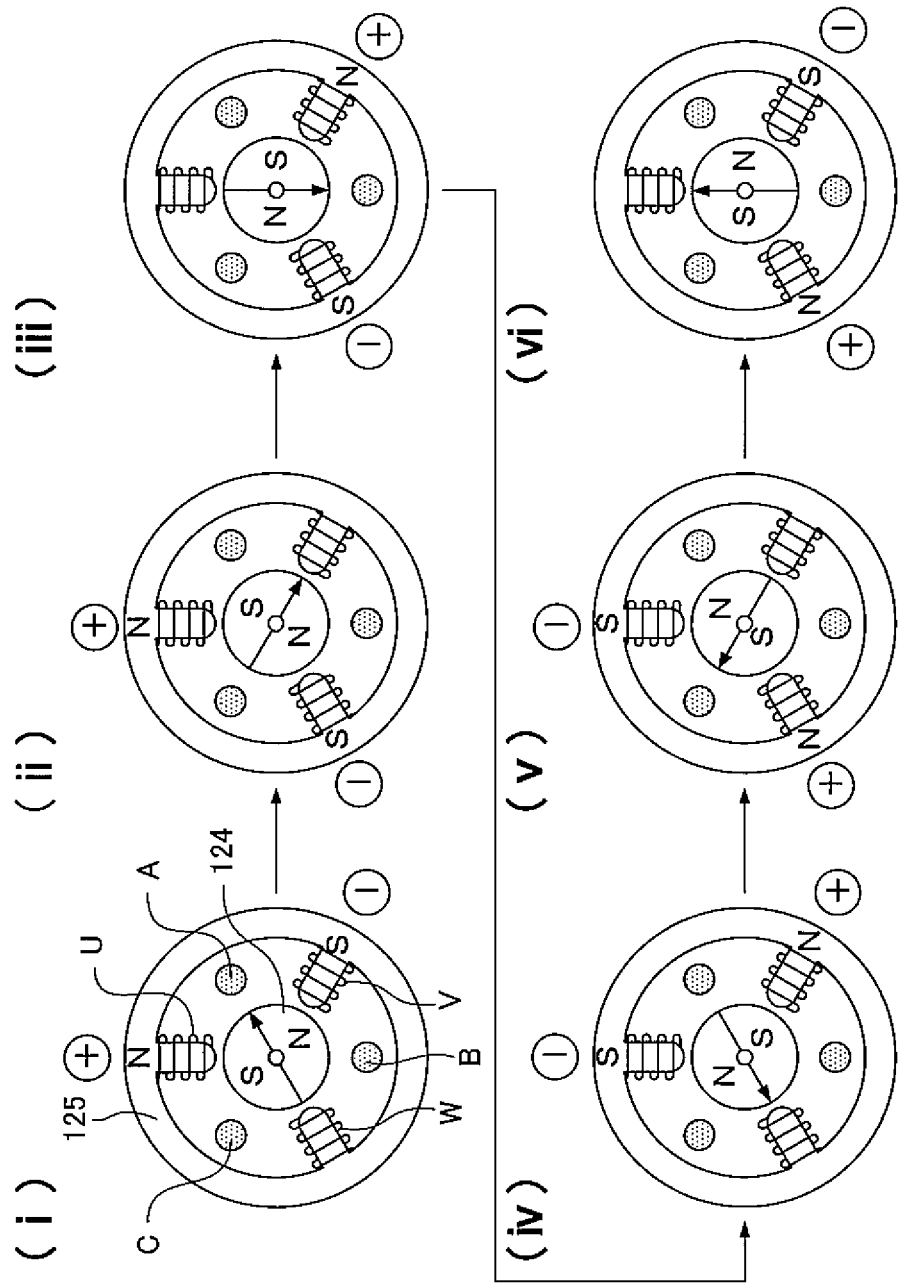
FIGS. 16(i)-(vi) are explanatory drawings showing the rotational driving states of the first motor according to the second embodiment.

FIG. 15 schematically shows connection when the first motor 71a is a three-phase brushless motor of outer rotor type. The first motor 71a includes a rotor 124 magnetized with two poles of a north pole and a south pole.

The first motor 71a further includes a stator 125 on which driving coils U, V, and W5 are wound. The driving coils U, V, and W make Y connections and are wound respectively on the three protrusions of the stator. The three protrusions are spaced at intervals of 120°.

Further, Hall elements A, B, and C are arranged so as to be displaced from the respective driving coils U, V, and W by 60°. The Hall elements detect the polarity (a north pole or a south pole) of the magnet field of the opposed rotor 124 and generate a signal at a level corresponding to the detected polarity. To be specific, an "H" level signal is generated at the detection of a north pole, and an "L" level signal is generated at the detection of a south pole. A controller 120 is made up of a rotor position detector 121 and a power driver 122.

When receiving a normal rotation command from a microcomputer 123, the rotor position detector 121 generates a driving signal pattern corresponding to one of six polarity patterns of the driving coils U, V, and W, in response to the output patterns of the Hall elements A, B, and C of the first motor 71a.

The driving signal pattern generated by the rotor position detector 121 is advanced to rotate the rotor 124, and an advanced rotating magnetic field is generated on the driving coils U, V, and W. Hence, the rotor 124 of the first motor 71a is rotated by an advanced rotating magnetic field during a normal operation.

The power driver 122 passes, through the driving coils U, V, and W, the exciting current of an energization pattern corresponding to the driving signal pattern generated by the rotor position detector 121. To be specific, the power driver 122 switches on/off the switching element according to the driving signal pattern generated by the rotor position detector 121, and switches the excitation phases of the stator of the first motor 71a. In other words, the power driver 122 applies a positive potential and a negative potential to the respective two-phase driving coils determined according to the driving signal pattern generated by the rotor position detector 121, and passes exciting current through the two-phase driving coils.

FIGS. 16(i) to 16(vi) show the relationship between the six polarity patterns of the driving coils U, V, and W and the position of the rotor 124. The driving coils U, V, and W are wound so as to be magnetized to a north pole at the application of a positive potential and magnetized to a south pole at the application of a negative potential. In this case, when a positive polarity phase fed with a positive potential, a negative polarity phase fed with a negative potential, and a phase not fed with exciting current are determined, the position of the rotor 124 is set at a location in one rotation of the rotor 124. In other words, the phases magnetized by the exciting current and the north pole and the south pole of the permanent magnet of the rotor 124 are attracted to each other in balance, so that the position of the rotor 124 is set. Further, the current position of the rotor 124 can be detected from the output patterns of the Hall elements A, B, and C.

During energization to the second motor 72a shown in FIG. 14, exciting current is not passed through any one of the driving coils U, V, and W of the first motor 71a. Mixing and agitation are laterally performed on the rotor 124 and the turntable 101 by swinging the lever 79.

When the control section 109 reversely rotates the third motor 73a to separate the second gear 80 from the first gear 74, the microcomputer 123 detects the current position of the rotor 124 from the output patterns of the Hall elements A, B, and C, and the exciting current is passed through the two proper phases of the driving coils U, V, and W, so that the turntable 101 and the analyzing device 1 are locked in the closest one of the states of FIGS. 16(i) to 16(vi). Thus it is possible to avoid a state in which a liquid such as a sample liquid in the analyzing device 1 moves from a predetermined position when the second gear 80 is separated from the first gear 74.

Alternatively, before the control section 109 rotates the third motor 73a in a forward direction to engage the second gear 80 with the first gear 74, the microcomputer 123 stores the current position of the rotor 124 by storing the output patterns of the Hall elements A, B, and C. When the control section 109 reversely rotates the third motor 73a to separate the second gear 80 from the first gear 74, the exciting current is passed through the two proper phases of the driving coils U, V, and W so as to generate patterns similar to the stored output patterns of the Hall elements A, B, and C, so that the position of the analyzing device 1 does not change before and after mixing and agitation. Thus it is possible to avoid a state in which a liquid such as a sample liquid in the analyzing device 1 moves from the predetermined position.

In the present embodiment, the lever 79 of the second drive part 72 is brought close to the turntable 101. In the agitation and swinging of the analyzing device 1, the turntable 101 may be brought close to the lever 79 of the second drive part 72 to cause the first and second gears 74 and 80 to mesh each other. Alternatively, in the agitation and swinging of the analyzing device 1, the turntable 101 of the first drive part 71 and the lever 79 of the second drive part 72 may be brought close to each other to cause the first and second gears 74 and 80 to mesh with each other. The analyzing device 1 can be agitated and swung by relatively moving the first drive part 71 and the second drive part 72 by the third drive part 73 to a position where the lever 79 and the turntable 101 are engaged with each other and a position where the lever 79 and the turntable 101 are not engaged with each other.

In the foregoing embodiments, the second drive part 72 is driven in engagement with the first gear 74 provided on the turntable 101. The first gear 74 may be formed on the outer periphery of an outer rotor 90 of the first motor 71a, and the second gear 80 of the second drive part 72 may mesh with the first gear 74. Alternatively, the swingingly driven second drive part 72 may come into contact with the outer periphery of the outer rotor 90 of the first motor 71a to laterally reciprocate the analyzing device 1 with respect to a rotation axis 107 with a predetermined amplitude range and a predetermined period.

Fourth Embodiment

Figure 17:
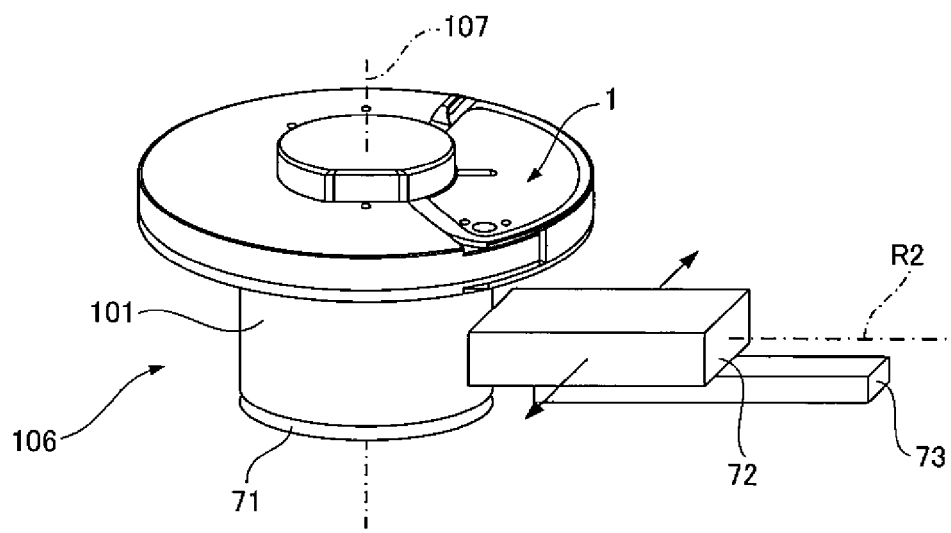
FIG. 17 is a perspective view showing a centrifugal separator according to a fourth embodiment of the present invention.
Figure 18:
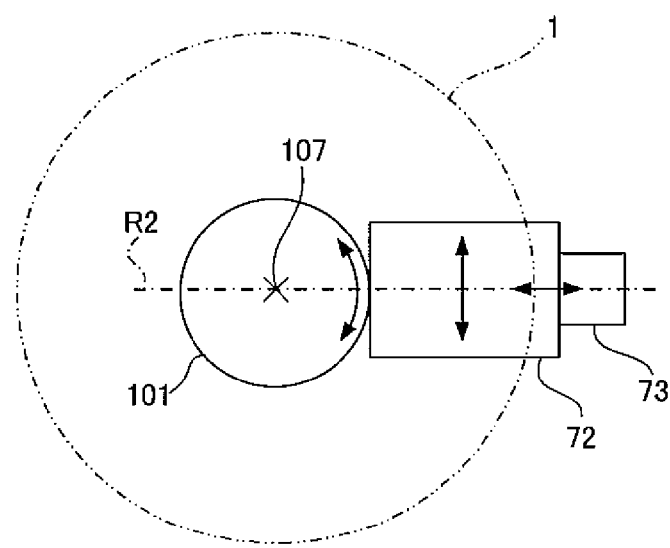
FIG. 18 is a top view of the centrifugal separator according to the fourth embodiment.

FIGS. 17 and 18 show a centrifugal separator installed in a blood analyzing apparatus according to the present invention. A door 103 of the blood analyzing apparatus is opened as in FIG. 5. An analyzing device 1 is set on a turntable 101 as in FIG. 6.

The analyzing device 1 has a passage for injecting a sample liquid such as blood and urine to perform centrifugal separation and agitation. On the top surface of the turntable 101, a groove 102 is formed. In a state in which the analyzing device 1 is set on the turntable 101, a rotary support part 115 formed on a cover substrate 4 of the analyzing device 1 and a rotary support part 116 formed on a protective cap 2 are engaged with the groove 102, so that the analyzing device 1 is stored.

After the analyzing device 1 is set on the turntable 101, the door 103 of the analyzing apparatus is closed before a rotation of the turntable 101, so that the set analyzing device 1 is pressed to the side of the turntable 101 by a movable piece 104 provided on the side of the door 103, by a biasing force of a spring 105 at a position on the rotation axis of the turntable 101. Thus the analyzing device 1 rotates together with the turntable 101 that is rotationally driven by a rotational drive section 106. Reference numeral 107 denotes the axis of rotation of the turntable 101.

As shown in FIGS. 17 and 18, the rotational drive section 106 is made up of a first drive part 71 for rotationally driving the turntable 101 about the rotation axis 107, a second drive part 72 that comes into contact with the turntable 101 and reciprocates in the tangential direction of the turntable 101 with respect to a vibration center R2 orthogonal to the rotation axis 107, and a third drive part 73 that brings the turntable 101 and the second drive part 72 into contact with each other only in agitation and separates the turntable 101 and the second drive part 72 during centrifugal separation. The third drive part 73 is made up of a power source such as a direct-current motor and an electromagnetic plunger. In order to efficiently transmit vibrations when the turntable 101 and the second drive part 72 are in contact with each other, the contact surfaces of the turntable 101 and the second drive part 72 may be made of a material having a high coefficient of friction or may have gear structures meshing with each other.

In a specific example of FIGS. 1 to 4, the contact surfaces of the second drive part 72 and the turntable 101 have gear structures meshing with each other and the third drive part 73 is made up of a direct-current motor.

The first drive part 71 for rotating the set analyzing device 1 is made up a first motor 71a and the turntable 101 that is mounted on the output shaft of the first motor 71a and has the analyzing device 1 set thereon. On the outer periphery of the turntable 101, a first gear 74 is formed. The first motor 71a is made up of a brushless motor of outer rotor type.

In addition to the first drive part 71, the rotational drive section 106 includes the second drive part 72 that is selectively engaged with the first drive part 71 and reciprocates the analyzing device 1 to laterally reciprocate the turntable 101 at a predetermined stop position with respect to the rotation axis 107 with a predetermined amplitude range and a predetermined period, and a third drive part 73 for relatively moving the first and second drive parts 71 and 72 to a position where the first and second drive parts 71 and 72 are engaged with each other (FIG. 1(b)) and a position where the first and second drive parts 71 and 72 are not engaged with each other (FIG. 1(a)).

The second drive part 72 and the third drive part 73 are configured as shown in FIGS. 2 to 4. On a chassis 75 where the first motor 71a is attached, a second motor 72a, a third motor 73a, and so on are attached. On a support table 77 attached to the chassis 75 so as to slide along an arrow 76 (see FIGS. 1(a) and 2), a support shaft 78 is mounted.

Further, a lever 79 is pivoted on the support shaft 78. On one end of the lever 79 on the side of the turntable 101, a second gear 80 is formed so as to mesh with the first gear 74 of the turntable 101. On the other end of the lever 79, a recessed portion 81 is formed. On the recessed portion 81, an eccentric cam 83 is engaged that is attached to an output shaft 82 of the second motor 72a. FIG. 4 is a plan view showing that the lever 79 has been removed from the support shaft 78.

With this configuration, when the second motor 72a is energized, the lever 79 swings between a solid line position and a virtual line position via the eccentric cam 83.

The lever 79 is urged by a helical spring (not shown) to reduce the backlash of the lever 79 during the swinging.

The third drive part 73 is made up of the third motor 73a attached to the chassis 75, a worm 85 attached to an output shaft 84 of the third motor 73a, a worm wheel 86 that is rotationally attached to the chassis 75 and meshes with the worm 85, and a rack 87 that is formed on the support table 77 and meshes with the worm wheel 86. Between the support table 77 and the chassis 75, an extension spring 88 is interposed to reduce backlash between the worm wheel 86 and the rack 87.

With this configuration, the third motor 73a is energized to rotate the worm wheel 86 along an arrow 89 (see FIG. 1(a)) until a detection switch 91 detects the support table 77 as shown in FIG. 1(b), so that the support table 77 on which the rack 87 meshes with the worm wheel 86 slides close to the turntable 101 and the second gear 80 of the lever 79 meshes with the first gear 74 of the turntable 101 as shown in FIG. 1(b). In this state, the second motor 72a kept energized enables the lever 79 to swingingly drive the turntable 101 in the tangential direction of the turntable 101. Thus by increasing the number of revolutions of the second motor 72a, acceleration high enough to agitate a small amount of fluid in the analyzing device 1 can be obtained even in a short time.

Figure 19:
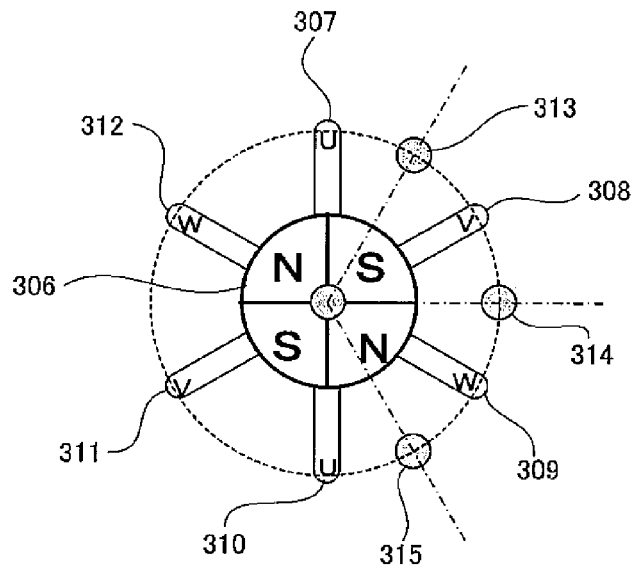
FIG. 19 is a principle diagram showing a quadrupole magnet three-phase brushless motor according to the fourth embodiment.

In FIG. 19, the first motor 71a is a quadrupole magnet three-phase brushless motor using a quadrupole magnet rotor 306, a U-phase driving coil 307, a V-phase driving coil 308, a W-phase driving coil 309, a U-phase driving coil 310, a V-phase driving coil 311, and a W-phase driving coil 312. The magnet rotor 306 has two pairs of north-pole and south-pole magnets. The driving coils 307, 308, 309, 310, 311, and 312 make Y connections and are wound on the respective six protrusions of a stator. The six protrusions are spaced at intervals of 60°.

The exciting currents of the three-phase driving coils are switched based on the detection of three Hall elements 313, 314, and 315 acting as magnetic sensors. The three Hall elements 313, 314, and 315 are arranged so as to be displaced from the respective three-phase driving coils U, V, and W by 30°. The Hall elements detect the polarity (a north pole or a south pole) of the magnetization of the opposed magnet rotor 306 and generate an electromotive force at a level corresponding to the detected polarity.

Figure 20:
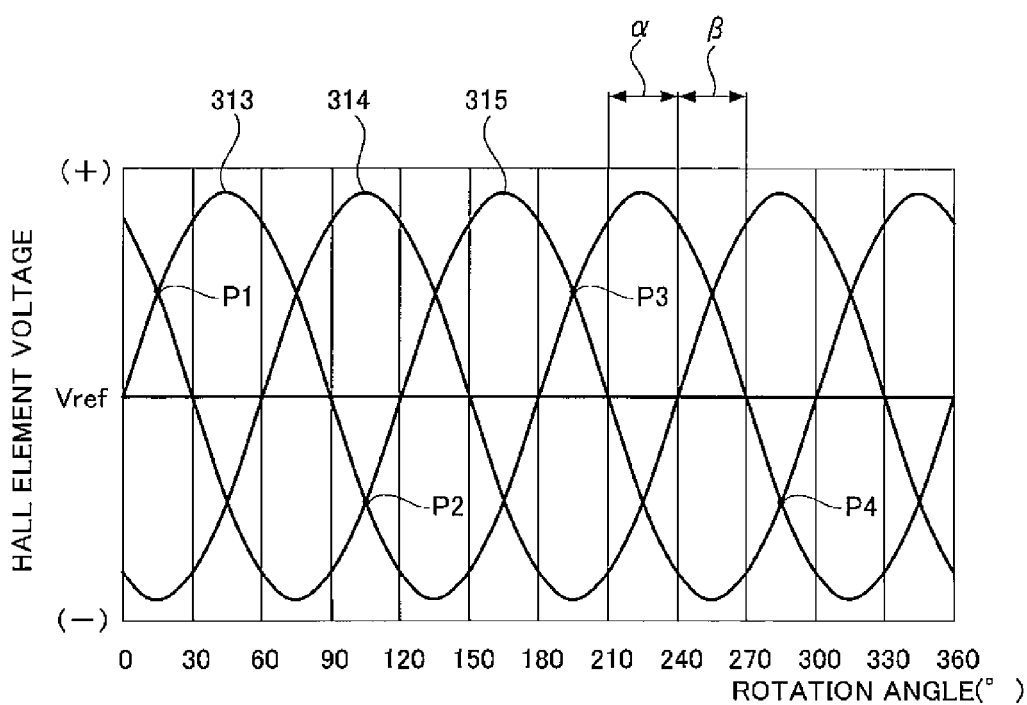
FIG. 20 is an angle characteristic diagram showing voltages outputted from the Hall elements of the quadrupole magnet three-phase brushless motor according to the fourth embodiment.

FIG. 20 shows the angular characteristics of voltages outputted from the Hall elements 313, 314, and 315 of the quadrupole magnet three-phase brushless motor. The horizontal axis represents a rotation angle when the magnet rotor has an angle of 0°. The vertical axis represents the output voltages of the Hall elements. The voltages from the Hall elements 313, 314, and 315 are outputted to the positive side relative to a reference voltage Vref when the north pole comes close to the Hall elements, and the voltages are outputted to the negative side when the south pole comes close to the elements. Since the magnet rotor 306 has the north and south poles arranged at intervals of 90°, the Hall element voltages each have a sinusoidal wave with a period of 180°. Further, the Hall elements 313, 314, and 315 are phase shifted by 60 mechanical degrees.

One of the output voltages of the Hall elements 313, 314, and 315 is inverted every 30° relative to Vref. Thus the output voltage is converted into a digital signal by a comparator circuit at a high level on the positive side and a low level on the negative side relative to Vref, so that a rotational position can be specified every 30° based on the output patterns of the Hall elements 313, 314, and 315. The output patterns of the Hall elements 313, 314, and 315 are used as the switching timing of the exciting currents of the three-phase driving coils.

Figure 21:
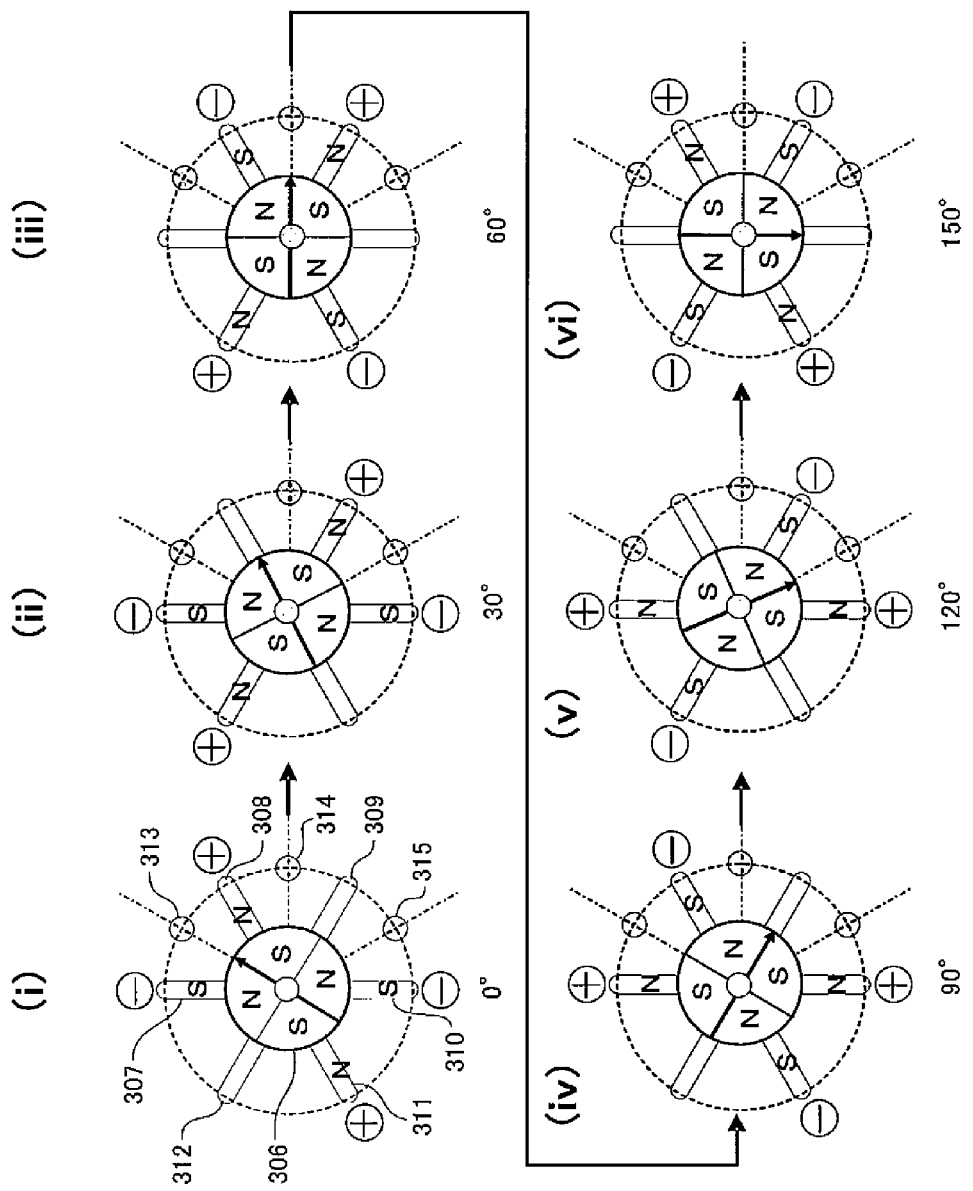
FIGS. 21(i)-(vi) show the relationship between the six polarity patterns of three-phase driving coils of the quadrupole magnet three-phase brushless motor and the position of a magnet rotor according to the fourth embodiment.

FIG. 21 shows the relationship between the six polarity patterns of the three-phase driving coils of the quadrupole magnet three-phase brushless motor and the position of the magnet rotor. The state of (i) is defined as an angle of 0°. The states of the magnet rotor 6 at intervals of 30° are shown in (i)→(ii)→(iii)→(iv)→(v)→(vi) and correspond to the rotation angles of FIG. 20. Of the three-driving coils of U phase, V phase, and W phase in Y connections, the V phase has a positive potential and the U phase has a negative potential in (i), so that exciting current passes from the V phase to the U phase, a north pole appears in the V phase, and a south pole appears in the U phase. Thus an attractive force and a repulsive force are generated on the magnet rotor 306 and the magnet rotor 306 is rotated clockwise by 30°. After the rotation of 30°, the polarity of the Hall element 315 is reversed in (ii). At this point, the W phase is set at a positive potential and the U phase is set at a negative potential, so that a north pole appears in the W phase, a south pole appears in the U phase, and the magnet rotor 306 is further rotated clockwise by 30°. After that, the magnet rotor 306 is rotated by changing the exciting coils as shown in (iii)→(iv)→(v)→(vi).

Figure 22:
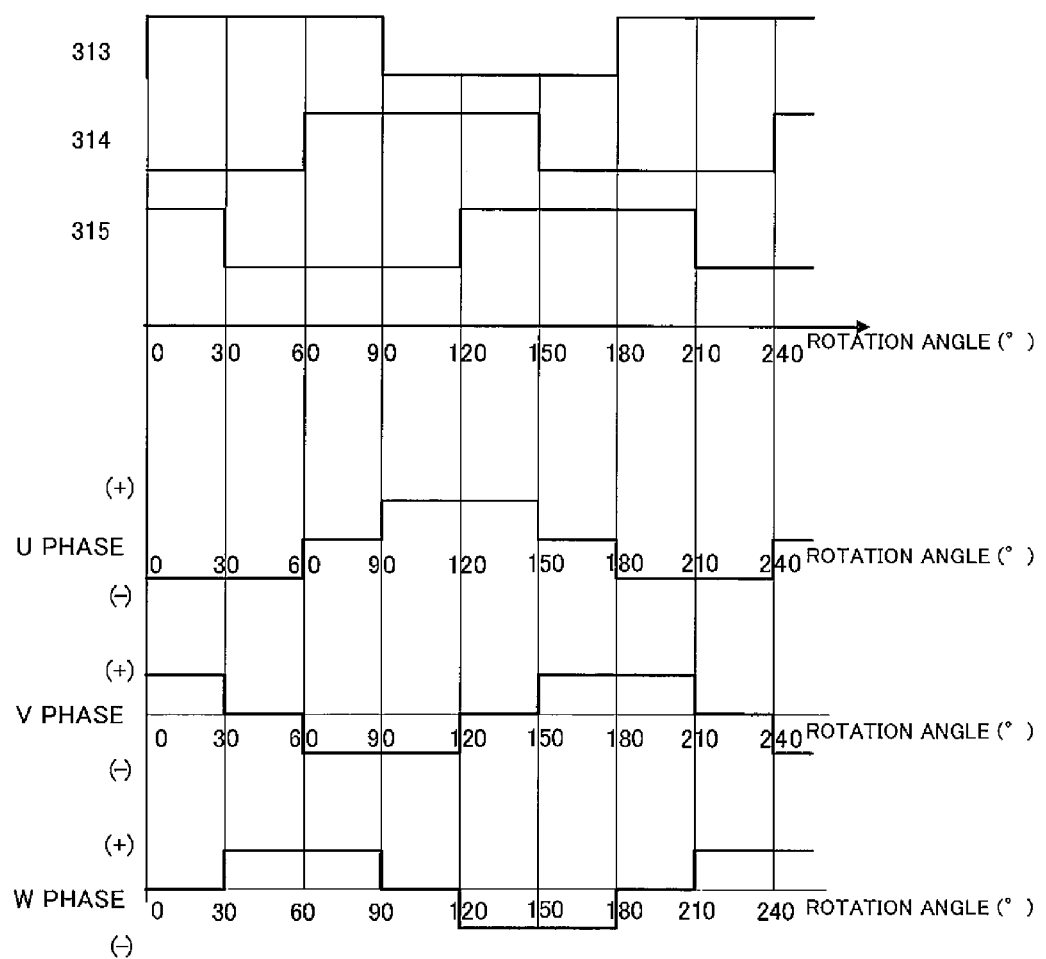
FIG. 22 shows the relationship between the states of energization to Hall elements 313, 314, and 315 and the driving coils of U phase, V phase, and W phase.
Figure 23:
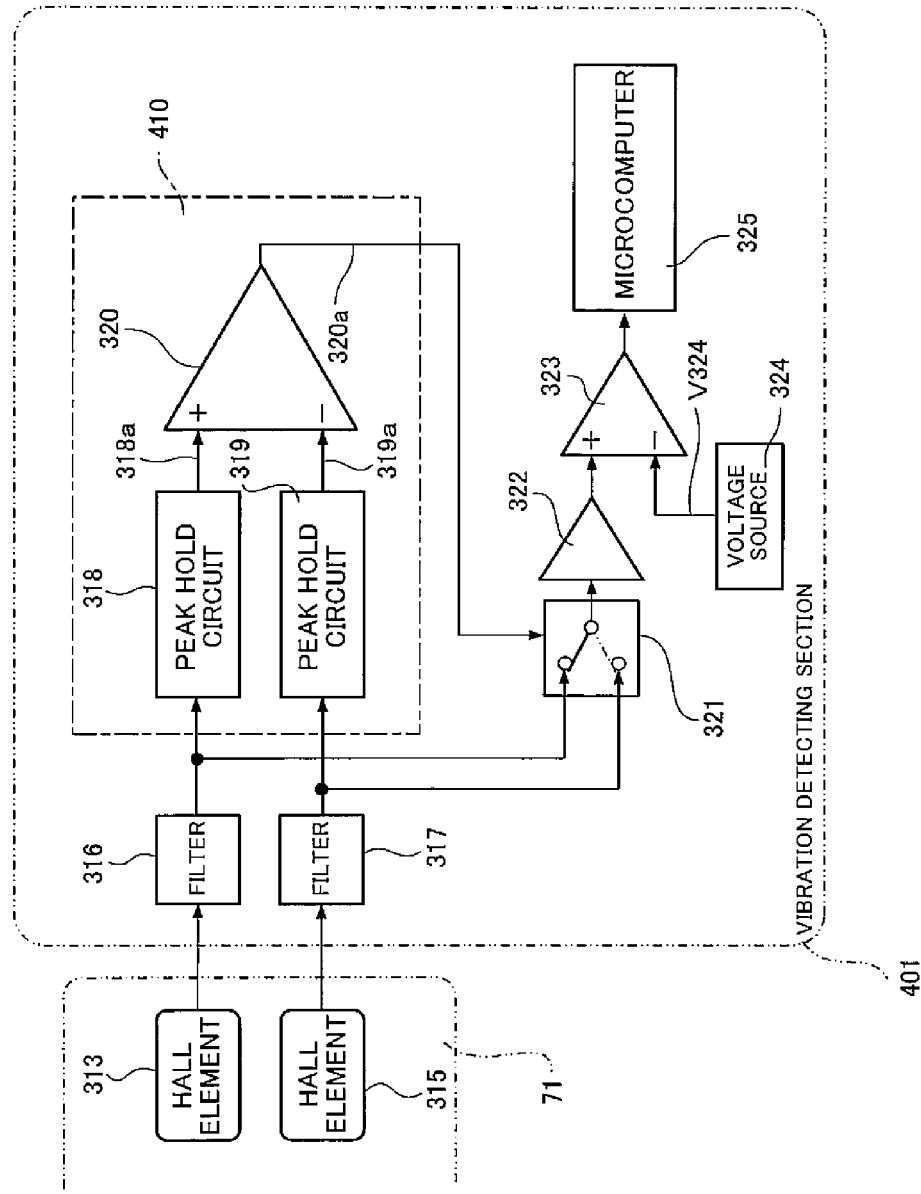
FIG. 23 is a structural diagram showing a vibration detecting section of the centrifugal separator according to the fourth embodiment.

FIG. 22 shows the states of energization to the Hall elements 313, 314, and 315 and the driving coils of U phase, V phase, and W phase. FIG. 23 shows a vibration detecting section 401 of the centrifugal separator.

In the centrifugal separator, a vibration frequency during agitation is detected based on the output signals of the Hall elements. In other words, even when the three-phase driving coils of the first motor 71a are not excited, vibrations transmitted to the turntable 101 by the second drive part 72 also vibrate the first motor 71a, so that the voltages of the three Hall elements 313, 314, and 315 fluctuate with the vibrations. The fluctuations are detected to specify a vibration frequency.

FIG. 23 shows an example in which the output voltages of the Hall elements 313 and 315 are extracted out of the three Hall elements. The output voltage of the Hall element 314 may be extracted.

The detection output of the Hall element 313 is connected to the non-inverting input (+) of a comparator 320 via a filter 316, which removes a direct-current signal from the output signal of the Hall element 313, and a peak hold circuit 318. The detection output of the Hall element 315 is connected to the inverting input (−) of the comparator 320 via a filter 317, which removes a direct-current signal from the output signal of the Hall element 315, and a peak hold circuit 319.

The filters 316 and 317 remove the direct-current signals from the input signals, extract the frequency components (alternating-current signals) of vibration frequencies, and output the frequency components. To be specific, the filters 316 and 317 are each made up of a bypass filter including a capacitor and a resistor. The capacitors of the filters 316 and 317 are placed in series with the respective output signals of the Hall elements 313 and 315 and the resistors are placed in parallel with the respective output signals.

The peak hold circuits 318 and 319 each hold the peak value of an inputted voltage and then output the voltage. To be specific, the peak hold circuits 318 and 319 each operate only in response to the input of a voltage larger than a previously inputted voltage, and hold the current input voltage for a certain period of time.

The comparator circuit 320 compares the output signals of the peak hold circuits 318 and 319. When the output signal of the peak hold circuit 318 is larger than that of the peak hold circuit 319, the comparator circuit 320 outputs a high-level control signal 320a. When the output signal of the peak hold circuit 318 is smaller than that of the peak hold circuit 319, the comparator circuit 320 outputs a low-level control signal 320a. In other words, the peak hold circuits 318 and 319 and the comparator circuit 320 constitute a first comparing section 410 for comparing the amplitudes of the output signals of the filters 316 and 317 and deciding which of the amplitude is larger.

The outputs of the filters 316 and 317 are connected to the non-inverting input (+) of a comparator circuit 323, which acts as a second comparing section, via an analog multiplexer 321 whose output states are switched in response to the control signal 320a outputted from the comparator circuit 320, and an alternating current amplifier circuit 322. The inverting input (−) of the comparator circuit 323 is fed with a threshold voltage V324 from a voltage source 324.

The analog multiplexer 321 selects one having a larger vibration amplitude out of the output signals of the two Hall elements 313 and 315, which are AC-coupled by the filters 316 and 317, based on the control signal 320a, and then the analog multiplexer 321 outputs the selected signal. The output signal of the analog multiplexer 321 is amplified in the alternating current amplifier circuit 322 to an amplitude enabling binarization, and is digitally converted in the comparator circuit 323 by the threshold voltage V324.

When the reference voltage is set at Vref after the direct-current signals are removed in the filters 316 and 317, the alternating-current signal is outputted with Vref serving as the amplitude center. Thus by setting the threshold voltage V324 at the same voltage as Vref, digital conversion can be performed at the amplitude center.

The output of the comparator circuit 323 is inputted to a microcomputer 325, and the vibration frequency of the turntable 101 is calculated by measuring a pulse period in the microcomputer 325.

Referring to FIGS. 24 to 27, the vibration detecting section 401 will be specifically described below.

Figure 24:
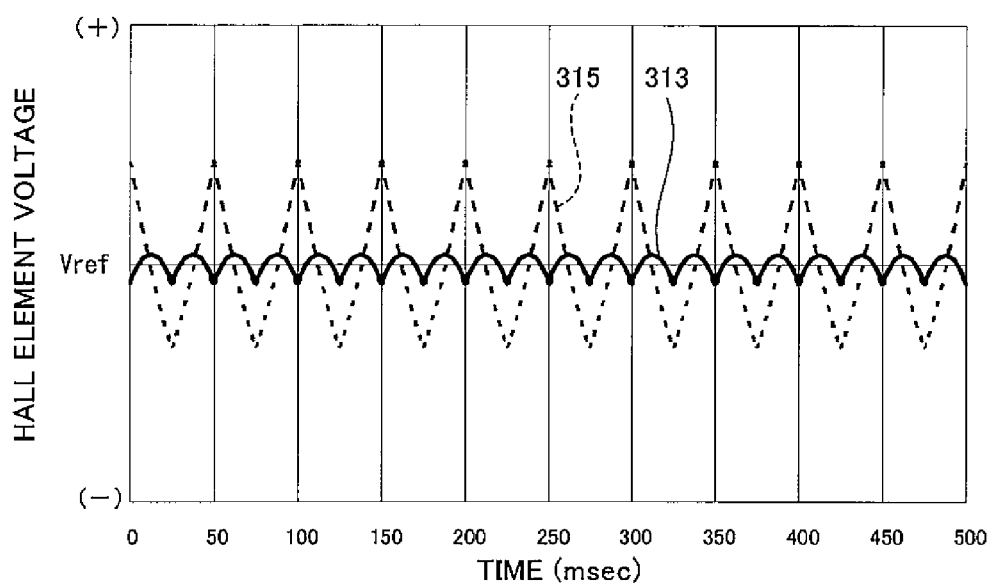
FIG. 24 is a characteristic diagram showing the output voltages of the AC-coupled Hall elements when the three-phase brushless motor is vibrated in the range of an angle α according to the fourth embodiment.
Figure 25:
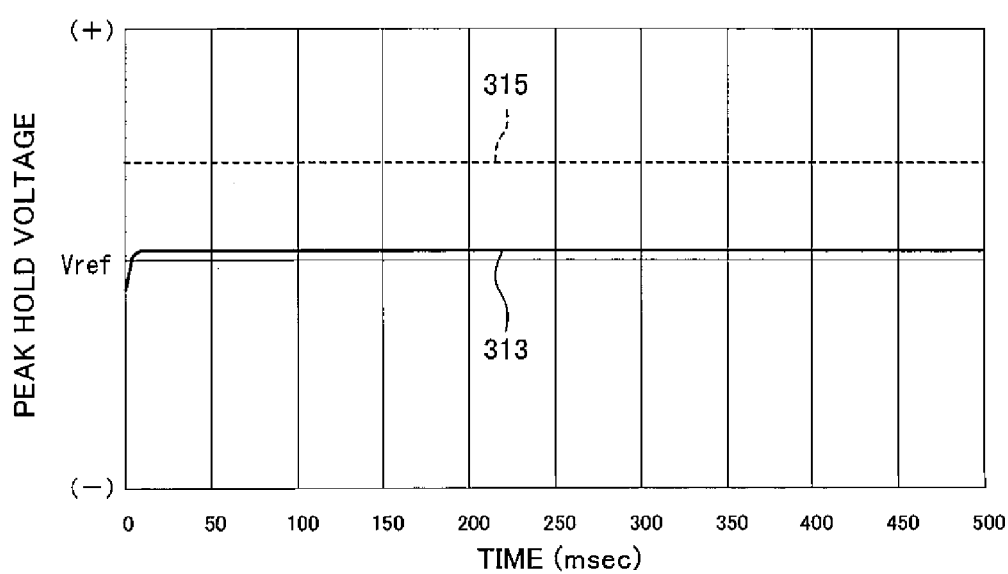
FIG. 25 is a characteristic diagram showing peak hold voltages when the three-phase brushless motor is vibrated in the range of the angle α according to the fourth embodiment.

FIG. 24 shows the time variations of the output voltages of the AC-coupled Hall elements when the quadrupole magnet three-phase brushless motor serving as the first drive part 71 is vibrated in the range of an angle α. FIG. 25 shows the time variations of the peak hold voltages in this case.

In the following explanation, it is assumed that the input/output characteristics of the comparator 320 exhibit no hysteresis.

In reciprocating vibrations at a frequency of 20 Hz in the range of the angle α, that is, from 210 mechanical degrees to 240 mechanical degrees, the vibrations cause fluctuations as shown in FIG. 24. At this angle, the signal from the Hall element 315 has a vibration frequency of 20 Hz that is a correct vibration frequency. However, the signal from the Hall element 313 vibrates around the peak of the sinusoidal wave, so that the vibration amplitude decreases and the vibration frequency is doubled. For this reason, a correct vibration frequency cannot be obtained.

In this case, as shown in FIG. 25, the Hall element 313 has a larger peak hold voltage than the Hall element 315. Thus the output of the Hall element 315 having a larger vibration amplitude can be selected in the analog multiplexer 321, so that the correct signal can be extracted based on the vibration frequency.

Figure 26:
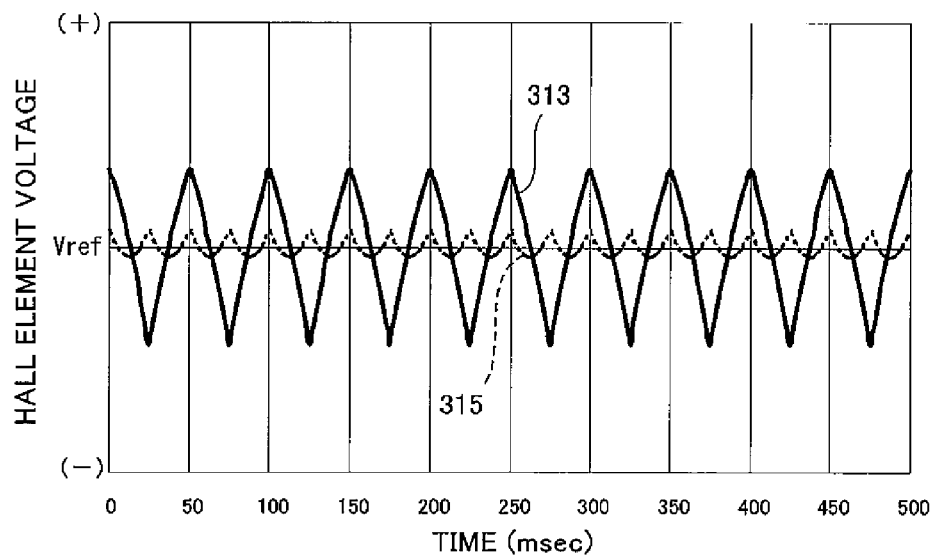
FIG. 26 is a characteristic diagram showing the output voltages of the AC-coupled Hall elements when the three-phase brushless motor is vibrated in the range of an angle β according to the fourth embodiment.
Figure 27:
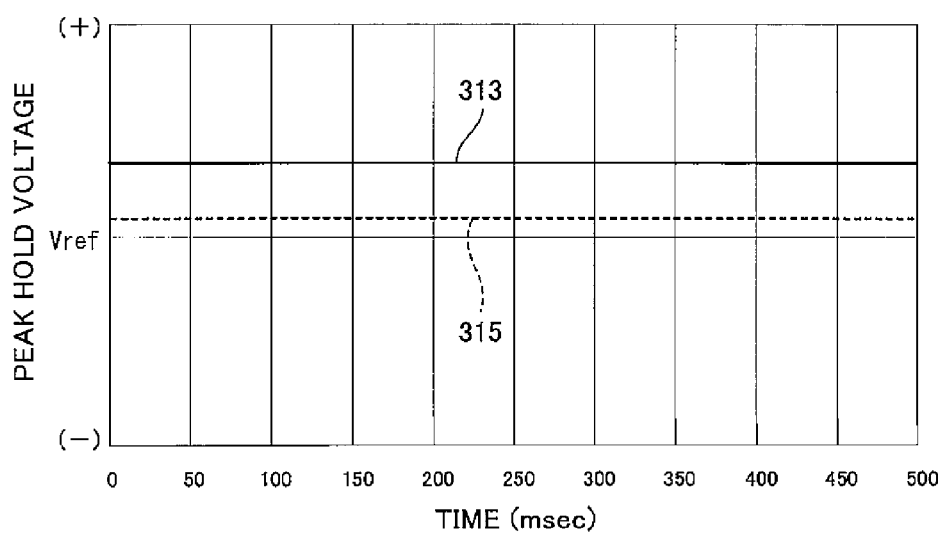
FIG. 27 is a characteristic diagram showing peak hold voltages when the three-phase brushless motor is vibrated in the range of the angle β according to the fourth embodiment.

FIG. 26 shows the time variations of the output voltages of the AC-coupled Hall elements when the quadrupole magnet three-phase brushless motor serving as the first drive part 71 is vibrated in the range of an angle β. FIG. 27 shows the time variations of the peak hold voltages in this case.

In this case, the states are reversed from those of FIGS. 24 and 25. In vibrations in the range of the angle β, a correct vibration frequency can be obtained from the Hall element 313 but a vibration frequency from the Hall element 315 is doubled. However, the signal from the Hall element 315 can be selected by comparing the peak hold voltages. Thus also in this case, the correct signal can be extracted based on the vibration frequency.

As previously mentioned, the brushless motor of Hall element type is used as the first drive part 71, the two Hall element signals 313 and 315 are extracted from the multiple Hall elements 313, 314, and 315 to compare the vibration amplitudes, and the signal having a larger vibration amplitude is extracted. This configuration can act as a centrifugal separator for centrifugal separation and a sensor for controlling agitation, thereby eliminating the need for providing a sensor for controlling agitation in addition to the first drive part 71.

The explanation described an example of the reciprocating vibrations of the turntable 101 from 210 mechanical degrees to 240 mechanical degrees and an example of the reciprocating vibrations of the turntable 101 from 240 mechanical degrees to 270 mechanical degrees. As shown in FIG. 20, the output signal of the Hall element 313 and the output signal of the Hall element 315 intersect at points P1, P2, P3, and P4. Thus the operations become unstable and a correct vibration frequency cannot be calculated in the reciprocating vibrations of the turntable 101 from 0 mechanical degrees to 30 mechanical degrees, in the reciprocating vibrations of the turntable 101 from 90 mechanical degrees to 120 mechanical degrees, in the reciprocating vibrations of the turntable 101 from 180 mechanical degrees to 210 mechanical degrees, and in the reciprocating vibrations of the turntable 101 from 270 mechanical degrees to 300 mechanical degrees.

Thus the comparator 320 of FIG. 23 has input/output characteristics exhibiting hysteresis.

Figure 28:
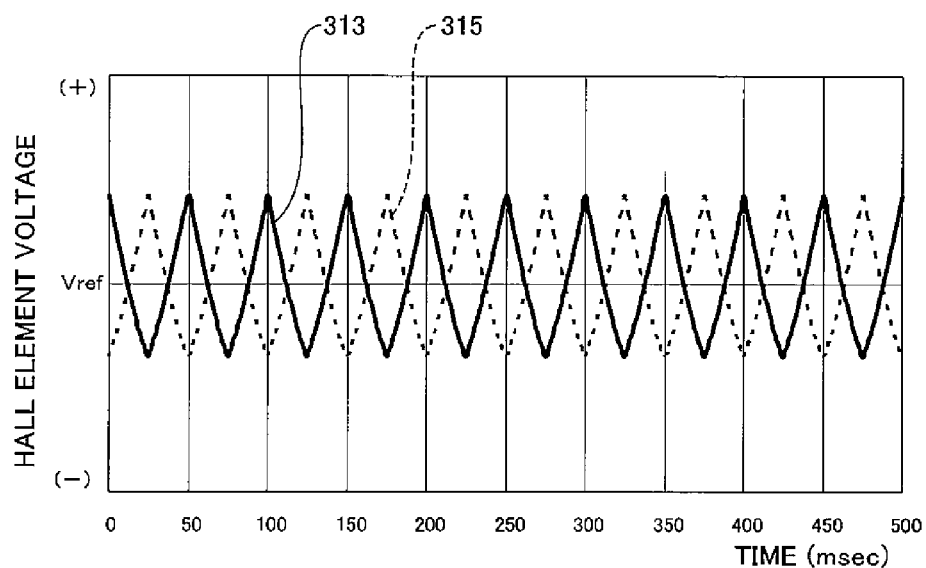
FIG. 28 is a characteristic diagram showing the output voltages of the AC-coupled Hall elements 313 and 315 in reciprocating vibrations with the vibration center disposed at the angle of one of points P1 to P4 shown in FIG. 20.
Figure 29:
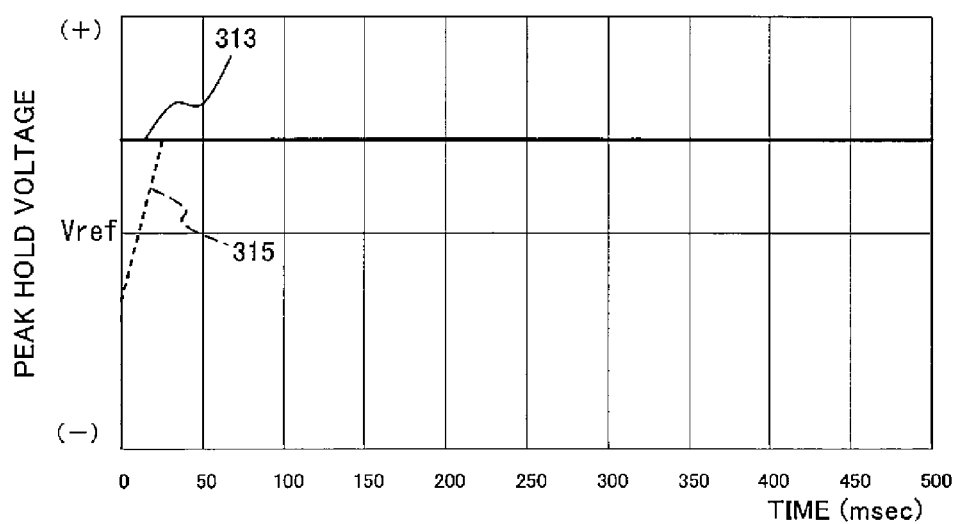
FIG. 29 is a characteristic diagram showing peak hold voltages according to the fourth embodiment.

FIG. 28 is a characteristic diagram showing the output voltages of the AC-coupled Hall elements 313 and 315 in the reciprocating vibrations of the turntable 101 with the vibration center disposed at the angle of one of the points P1 to P4 shown in FIG. 20. FIG. 29 is a characteristic diagram showing the peak hold voltages.

As shown in FIG. 28, in vibrations around P1 to P4 of FIG. 20, the output signals of the Hall elements 313 and 315 are in opposite phase and have the vibration amplitudes at the same level.

As shown in FIG. 29, the Hall element 313 has a larger peak hold voltage immediately after the start of vibrations but the peak hold voltage of the Hall element 315 increases with the passage of time. Finally, the peak hold voltages of the Hall elements 313 and 315 are kept at the same level.

Figure 30:
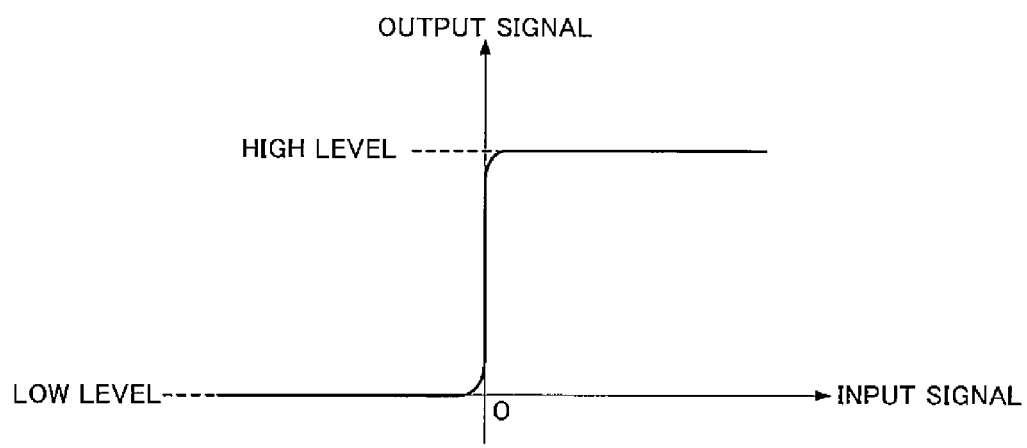
FIG. 30 is an input/output characteristic diagram of a comparator circuit 320 according to the fourth embodiment.

FIG. 30 is an input/output characteristic diagram of the comparator circuit 320. The horizontal axis represents a value obtained by subtracting the output of the peak hold 19 from the output of the peak hold circuit 318, and the vertical axis represents the output signal.

When the peak hold voltages are kept at the same level as shown in FIG. 29, the input signal of the comparator circuit 320 becomes zero and the output signal produces chattering. Since the output signals of the Hall elements 313 and 315 are in opposite phase, chattering that switches the selection signal of the analog multiplexer 321 causes phase inversion, so that a vibration frequency is erroneously detected.

Figure 31:
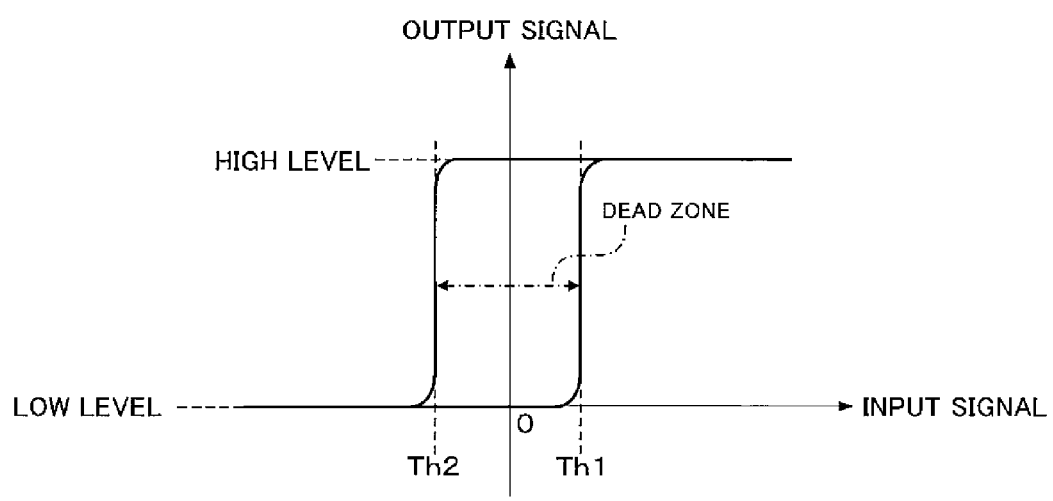
FIG. 31 is an input/output characteristic diagram when a hysteresis characteristic is provided for the comparator circuit 320 according to the fourth embodiment.

The problem of erroneous detection can be solved by providing a hysteresis characteristic for the comparator circuit 320. FIG. 31 is an input/output characteristic diagram when the hysteresis characteristic is provided for the comparator circuit 320. The horizontal axis represents an input signal obtained by subtracting the peak hold circuit 319 from the peak hold circuit 318, and the vertical axis represents the output signal.

A comparison between FIGS. 30 and 31 proves that when the comparator circuit 320 does not have a hysteresis characteristic, a high level and a low level are switched as shown in FIG. 30 at "0" level serving as a threshold value, whereas the comparator circuit 320 is provided with a hysteresis characteristic so as to have a first threshold value Th1 where the output signal is at high level and a second threshold value Th2 where the output signal is at low level. In this case, a dead zone (Th1-Th2) of FIG. 31 is formed where the output is not changed by fluctuations of the input signal and an output fixed at one of high level and low level is hardly inverted.

To be specific, in FIG. 29, the peak hold voltage of the Hall element 313 is larger than that of the Hall element 315 immediately after the start of vibrations, the input of the comparator circuit 320 reaches at least the first threshold value Th1, and the input of the comparator circuit 320 is fixed at high level. After that, the peak hold voltages of the Hall elements 313 and 315 are at the same level and thus the input of the comparator circuit 320 becomes "0". However, the input of the comparator circuit 320 does not decrease to the second threshold value Th2 or less and thus is not switched to low level.

Thus the selection of the analog multiplexer 321 in response to the control signal 320a of the comparator circuit 320 is kept at one of the Hall elements 313 and 315 and the comparator circuit 320 is not switched during vibrations, so that the vibration frequency can be accurately detected.

Figure 32:
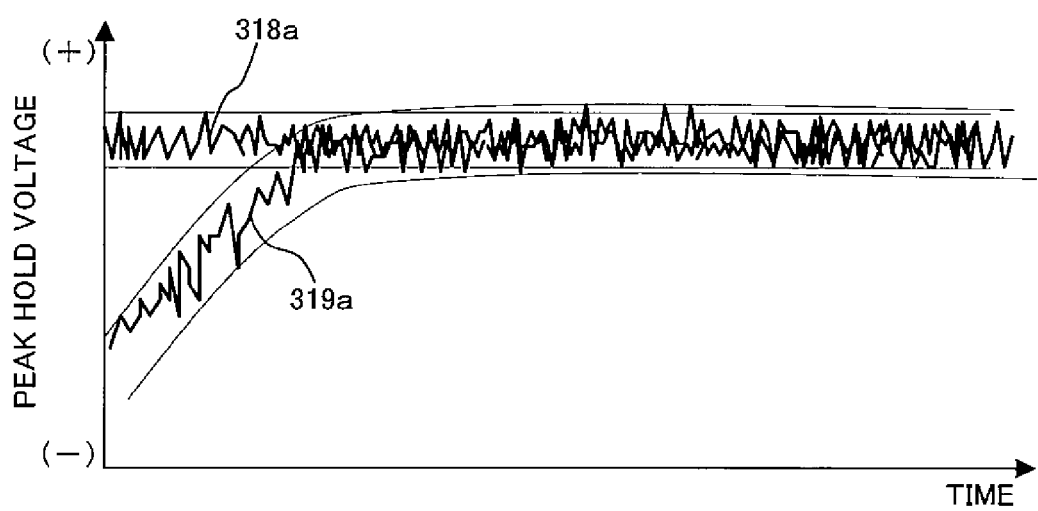
FIG. 32 is an enlarged view of a vertical axis (voltage range) of FIG. 29 according to the fourth embodiment.

The dead zone (Th1-Th2) where the control signal 320a is not switched by the noise amplitudes of the output signals of the two peak hold circuits 318 and 319. FIG. 32 is an enlarged view of the vertical axis (voltage range) of FIG. 29. When the dead zone (Th1-Th2) is smaller than the noise amplitudes of output signals 318a and 319a of the two peak hold circuits 318 and 319, the comparator is switched in response to noise. Thus it is desirable to provide the dead zone (Th1-Th2) at least twice the noise amplitudes.

Fifth Embodiment

Figure 33:
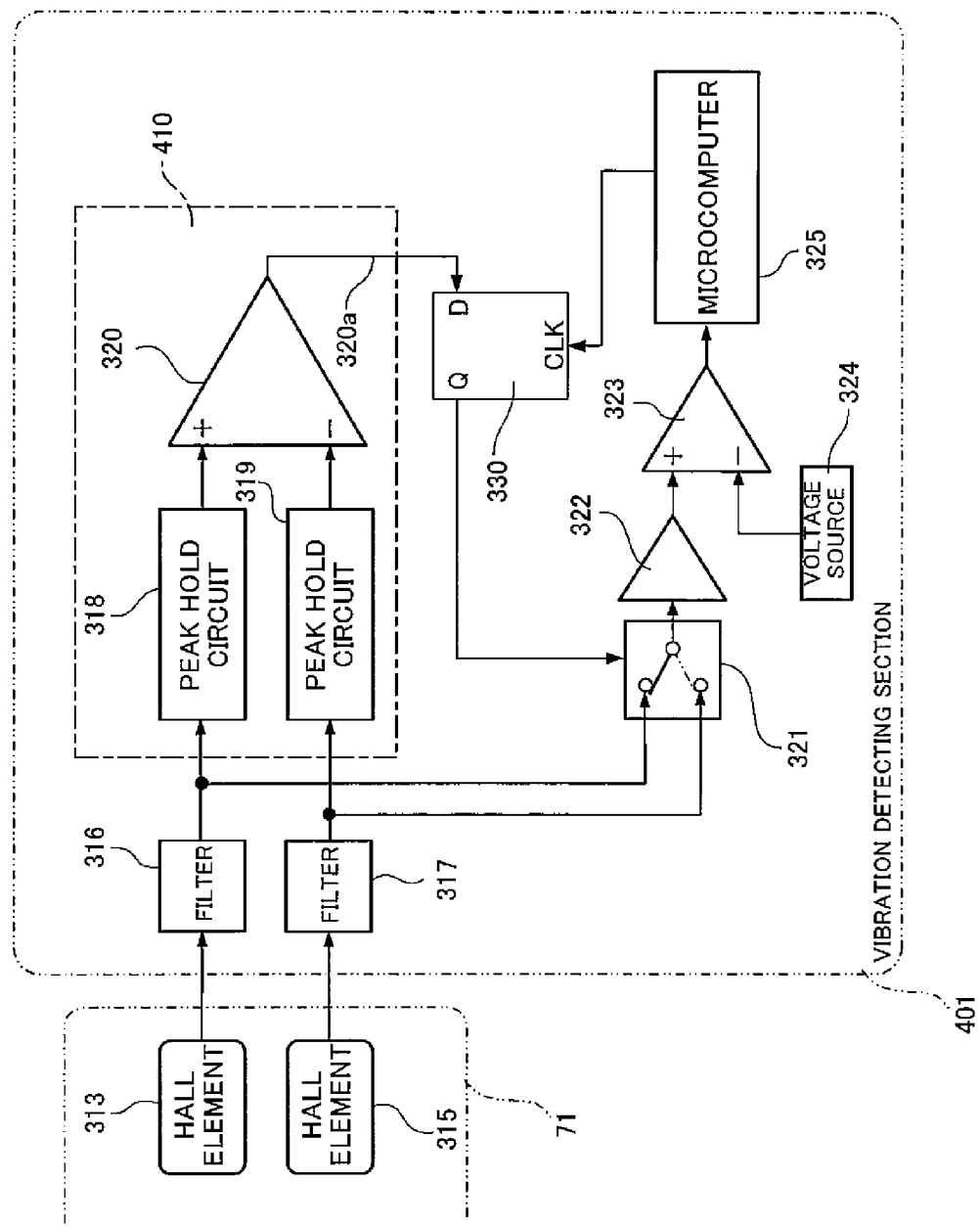
FIG. 33 is a structural diagram showing a vibration detecting section 401 according to a fifth embodiment of the present invention.

FIG. 33 shows a vibration detecting section 401 of a centrifugal separator according to a fifth embodiment of the present invention.

In FIG. 23 showing the fourth embodiment, the comparator circuit 320 is provided with the hysteresis characteristic, so that a correct vibration frequency can be calculated regardless of the position of the turntable 101 vibrated in a reciprocating manner. In the vibration detecting section 401 of FIG. 33, instead of a hysteresis characteristic for a comparator circuit 320, a D flip-flop 330 is provided as a latch. Other configurations are the same as those of the fourth embodiment.

The D flip-flop 330 has an input terminal D fed with a control signal 32a, and the switching state of an analog multiplexer 321 is controlled by a signal from an output terminal Q of the D flip-flop 330.

The D flip-flop 330 outputs the signal level of the input terminal D to the output terminal Q at a rising edge of a digital signal inputted from a microcomputer 325 to a clock terminal CLK. The output of the output terminal Q is kept until another rising edge is inputted to the clock terminal CLK.

After the start of vibrations, a pulse is transmitted from the microcomputer 325 to the clock terminal CLK of the D flip-flop 330 and the control signal at that time is held in the analog multiplexer 321. Thus even when the control signal 320a is switched, the selection state of the analog multiplexer 321 is not switched, thereby achieving the same effect as the hysteresis characteristic.

Sixth Embodiment

Figure 34:
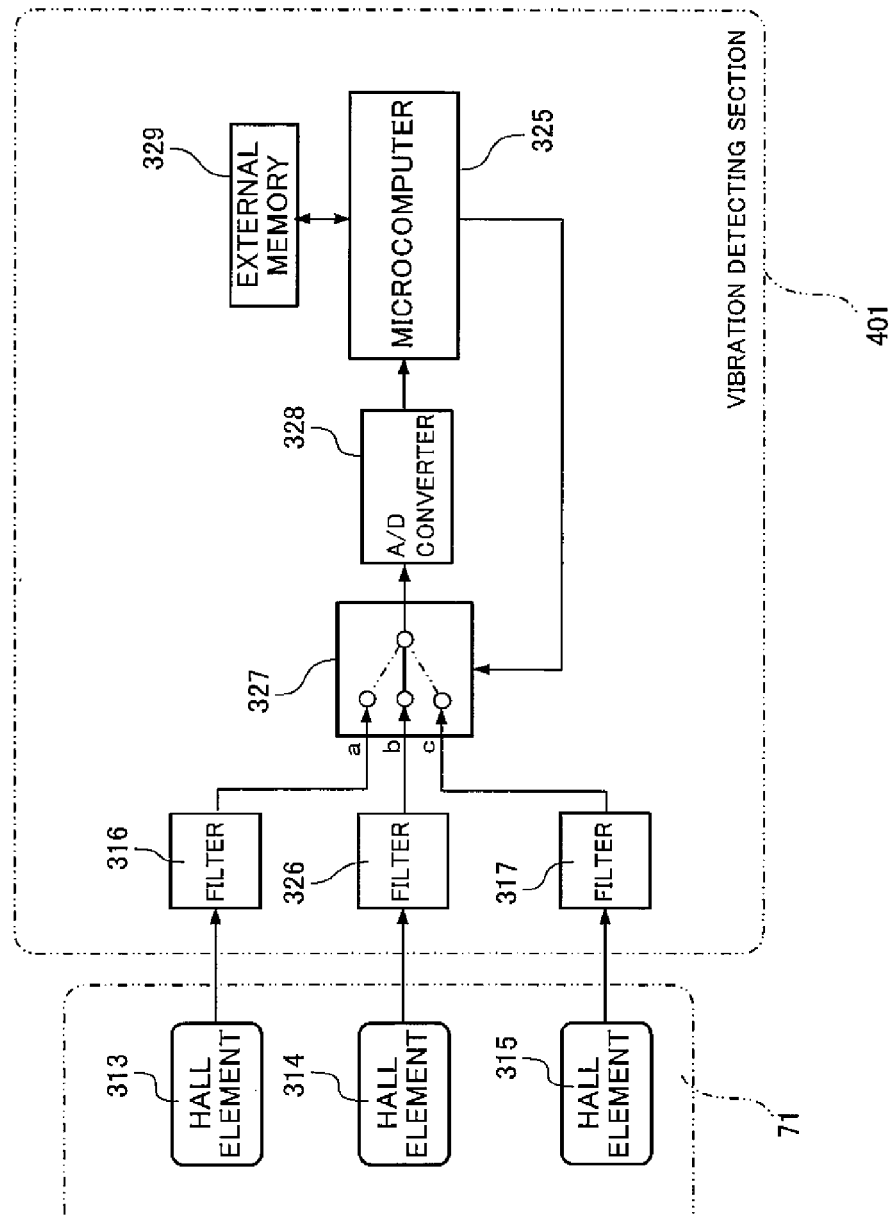
FIG. 34 is a structural diagram showing a vibration detecting section of a centrifugal separator according to a sixth embodiment of the present invention.
Figure 35:
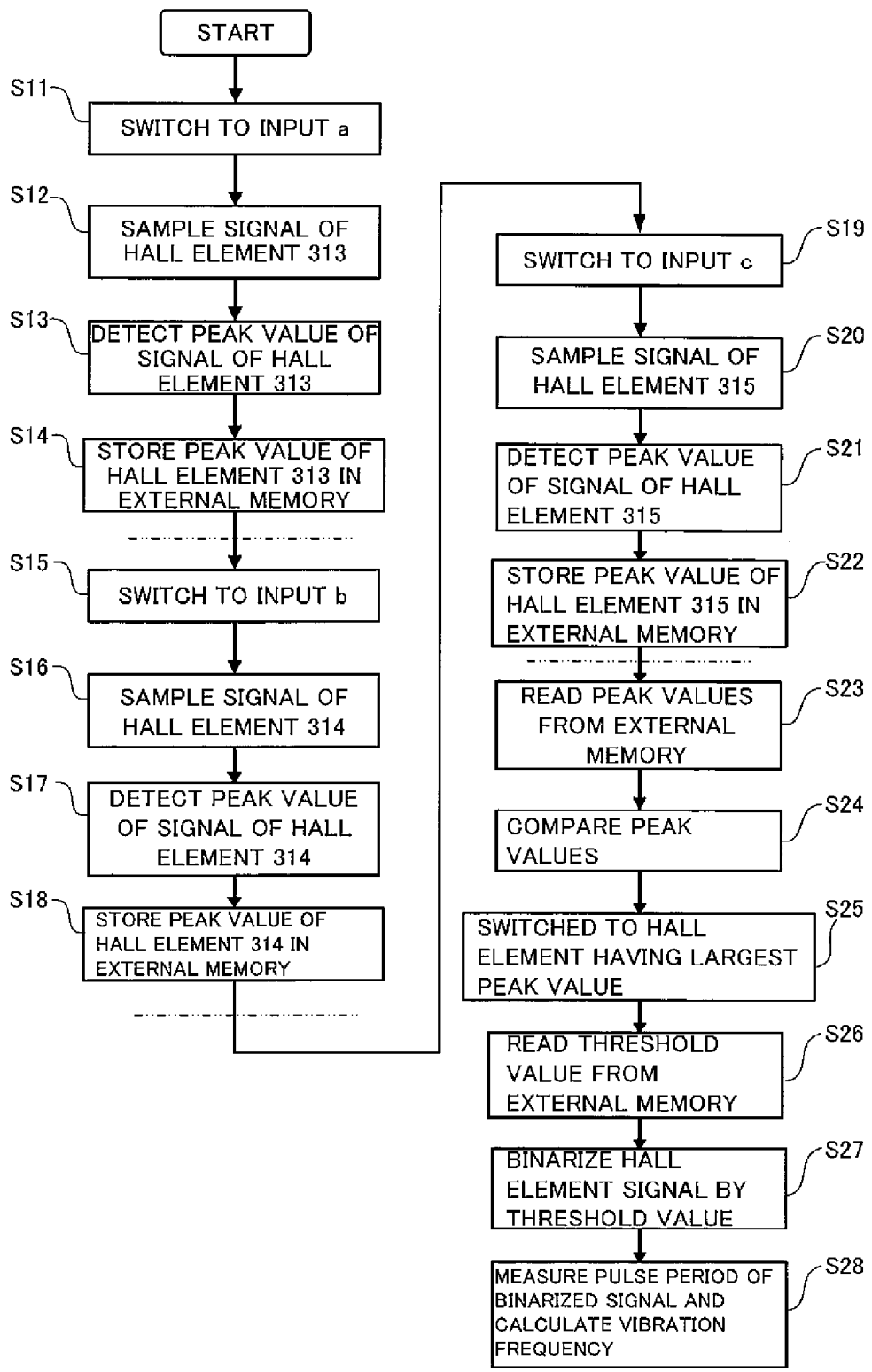
FIG. 35 is a process drawing showing the detection of a vibration frequency of a microcomputer according to the sixth embodiment.

FIGS. 34 and 35 show a vibration detecting section 401 of a centrifugal separator according to a sixth embodiment of the present invention.

In FIG. 23 showing the fourth embodiment, a vibration frequency is calculated using the outputs of the two Hall elements 313 and 315 as input signals. FIG. 34 is different from the fourth embodiment in that a vibration frequency is calculated using the outputs of three Hall elements 313, 314, and 315 as input signals. To be specific, FIG. 34 is different from the fourth embodiment in that a three-to-one analog multiplexer 327 is provided to extract the outputs of the three Hall elements and an analog-to-digital converter 328 is provided to replace signal processing performed by a peak detection circuit and a comparator with numerical calculation performed by a microcomputer 325.

In FIG. 34, reference numeral 327 denotes the three-to-one analog multiplexer that has three circuits a, b, and c on the input and one circuit on the output. The input of the three-to-one analog multiplexer 327 receives the outputs of the Hall elements 313, 314, and 315 through filters 316, 326, and 317. The analog multiplexer 327 is controlled by a signal from the microcomputer 325. For example, when receiving a 2-bit signal of "00" from the microcomputer 325, the analog multiplexer 327 selects "input a". When receiving "01", the analog multiplexer 327 selects "input b". When receiving "10", the analog multiplexer 327 selects "input c". The output of the analog multiplexer 327 is converted to a multilevel signal in the analog-to-digital converter 328 and is transferred to the microcomputer 325. External memory 329 is made up of volatile memory such as SRAM and nonvolatile memory such as EEPROM and bidirectionally communicates stored data with the microcomputer 325.

FIG. 35 is a process drawing showing the detection of the vibration frequency of the microcomputer 325.

In the following explanation, "set" is a state in which a second drive part 72 is engaged with a turntable 101 and "start" is timing when vibration and agitation are started after the setting.

First, in step S11, the output of the analog multiplexer 327 is switched to the selection state of "input a".

In step S12, a fixed number of output signals from the Hall element 313 are sampled from the output of the analog-to-digital converter 328.

In step S13, a peak value is detected from the output signals from the Hall element 313 after the output signals are sampled in step S12.

In step S14, the peak value detected in step S13 is stored in the external memory 329.

Next, in step S15, the output of the analog multiplexer 327 is switched to the selection state of "input b". In steps S16 to S18, output signals from the Hall element 314 are processed as in steps S12 to S14.

After that, in step S19, the output of the analog multiplexer 327 is switched to the selection state of "input c". In steps S20 to S22, output signals from the Hall element 315 are processed as in steps S12 to S14.

Next, in step S23, the peak values of the Hall element 313, 314, and 315 in the external memory 29 are read and compared with one another in step S24.

In step S25, the switching state of the analog multiplexer 327 is fixed based on the comparison result of the peak values in step 24 until an operation of vibration and agitation is completed.

The comparison result of the peak values in step 24 has three patterns of case 1 to case 3 as follows:

Case 1: Hall element 313=Hall element 314>Hall element 315

Case 2: Hall element 314=Hall element 315>Hall element 313

Case 3: Hall element 315=Hall element 313>Hall element 314

To be specific, in Case 1, the switching state of the multiplexer 327 is fixed at a switching state for the selection and output of the Hall element 313. In Case 2, the switching state of the multiplexer 327 is fixed at a switching state for the selection and output of the Hall element 314. In Case 3, the switching state of the multiplexer 327 is fixed at a switching state for the selection and output of the Hall element 315.

In step S26, a threshold value is read from the external memory 329.

In step S27, the output signals of the Hall elements are binarized by processing the output of the analog multiplexer 327 at the threshold value read in step S26.

In step S28, the pulse period of the signal binarized in step S27 is measured and a vibration frequency is calculated.

In this way, vibration amplitudes from the three Hall elements are compared with one another and the Hall element having the largest vibration amplitude is extracted in the sixth embodiment. This configuration can achieve higher detection accuracy of a vibration frequency than in the fourth embodiment in which the two Hall elements are compared with each other. Further, the replacement with the numerical calculation in the microcomputer 325 can simplify the configuration.

In the case where the turntable 101 is vibrated again with the same mechanical degrees, the switching state of the analog multiplexer 327 in step S25 is stored beforehand. The stored switching state is read thereafter to have the same switching state in the analog multiplexer 327. Thus only by repeating a routine of steps S26 to S28, the vibration frequency of the turntable 101 can be calculated.

In the foregoing embodiments, the quadrupole magnet three-phase brushless motor is used. Any kind of brushless motor is applicable as long as multiple Hall elements are used to detect a rotational position.

In the foregoing embodiments, the microcomputer 325 is provided with a routine for confirming whether a vibration frequency calculated by the microcomputer 325 is a specified value or not. The microcomputer 325 detects a state in which the vibration frequency does not reach the specified value, and notifies a user of the occurrence of the state, thereby preventing a reduction in the analysis accuracy of a blood component.

Seventh Embodiment

Figure 36:
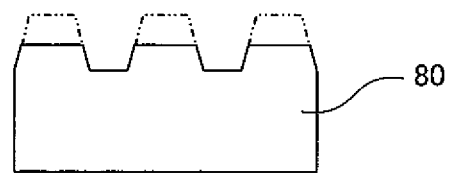
FIG. 36 is an enlarged view showing a second gear to explain a problem according to a seventh embodiment of the present invention.

As described in the first and third embodiments, when the second gear 80 is meshed with the first gear 74 to reciprocate the turntable 101, the long-term operation of the analyzing apparatus wears the second gear 80 and deforms the original shapes of the teeth from virtual lines to solid lines as shown in FIG. 36.

The worn second gear 80 may change a frequency for swinging performed to agitate a small amount of fluid in the analyzing device set on the turntable 101, so that the analysis accuracy may not be maintained. In a seventh embodiment for solving the problem, an analyzing apparatus is provided that includes a rotational drive section capable of stably swinging even in the case of deformation such as the wearing of a component when the rotational drive section reciprocates a turntable in engagement with the turntable on which the analyzing device is set.

First, mechanical configurations such as an analyzing device 1 used for analysis and a rotational drive section 106 including a turntable 101 are identical to the configurations of the first embodiment.

In the analyzing process of an analyzing apparatus 100, the turntable 101 is rotated at high speed by a first motor 71a and a sample liquid is transferred to a measuring chamber 40 of the analyzing device 1. At some point of this period, in order to temporarily stop the driving of the first motor 71a and swing the analyzing device 1, a second gear 80 is brought close to the turntable 101 by operating the third motor 73a and a second motor 72a is operated.

In this example, the second motor 72a is a direct-current motor and the rotation speed varies with an applied voltage.

After that, when the sample solution obtained by diluting a specific component of the sample liquid with a diluent reaches the measuring chamber 40, the driving of the first motor 71a is temporarily stopped and the second motor 72a is operated to swing the analyzing device 1, so that the sample solution and a reagent set in the measuring chamber 40 are agitated and a reaction occurs.

And then, the first motor 71a rotates the turntable 101 at high speed again; meanwhile, detection light having passed through the solution of the measuring chamber 40 from a light source 112 is read by a photodetector 113, so that the component is read.

Figure 38:
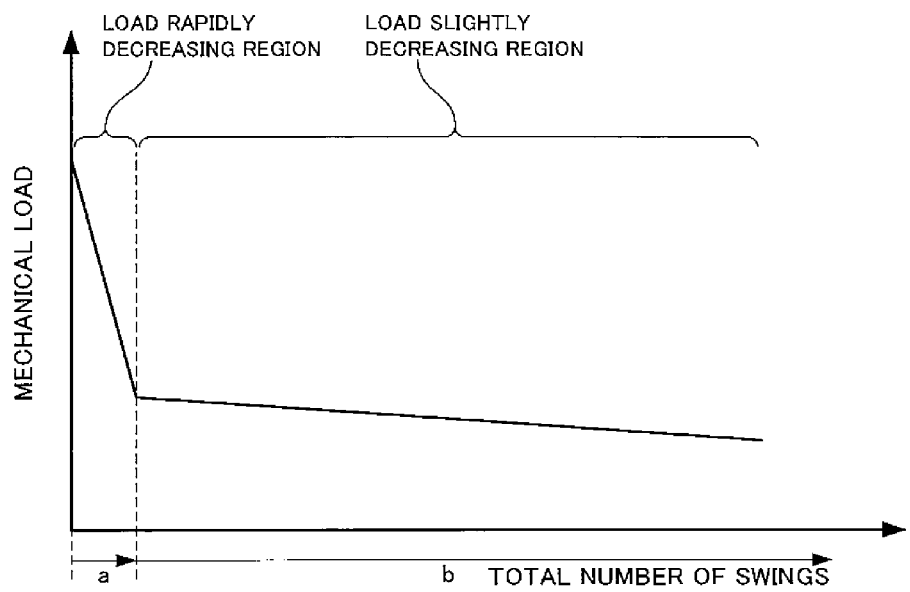
FIG. 38 shows the relationship between the total number of swings of the rotational drive section and a change of a mechanical load.

As a result of repeated swinging, 81, 83 and members constituting a swinging mechanism around 81 and 83 become more slidable owing to the lubrication of applied grease immediately after the start of use of the analyzing apparatus 100, and the load of the second motor 72a rapidly decreases as indicated by a region a (load rapidly decreasing region) of FIG. 38. Thus even when a voltage applied to the second motor 72a is kept constant, the swinging frequency of the analyzing device 1 fluctuates and the contents of agitation become unstable.

Figure 39:
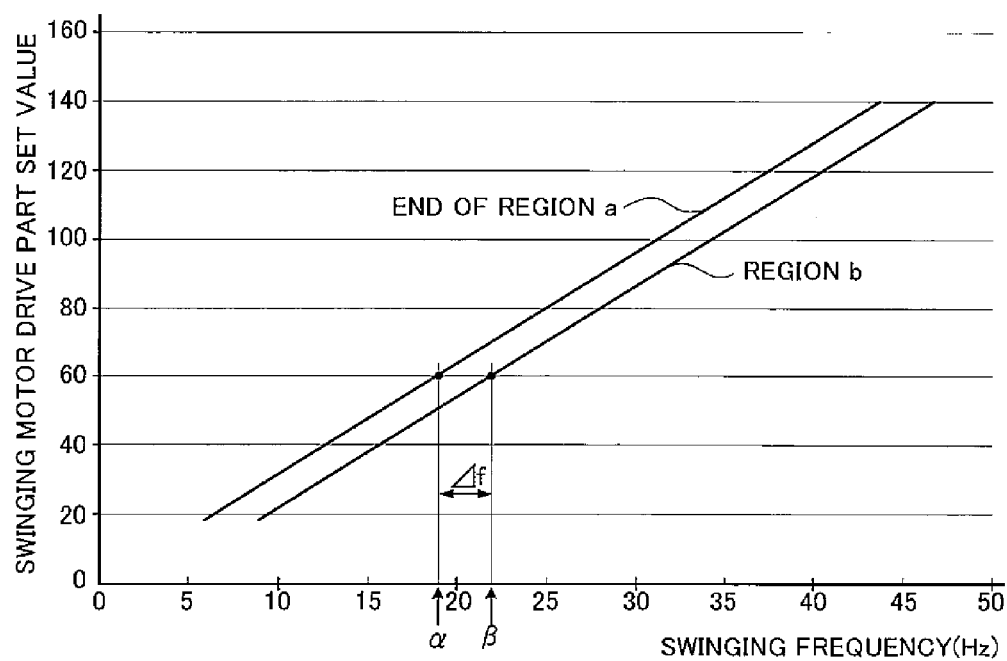
FIG. 39 shows the relationship between a set value for a swinging motor drive part of the rotational drive section and a swinging frequency.

After the end of the region a, the second gear 80 wears, the engagement with a first gear 74 gradually decreases, and the load of the second motor 72a gradually declines as indicated by a region b (load slightly decreasing region). Thus as shown in FIG. 39, a swinging frequency in a period of the region b is increased by Δf (in FIG. 39, the swinging frequency is increased by +4 Hz from α to β) as compared with a characteristic at the end point of the region a, so that the contents of agitation are not stabilized even in the region b.

Figure 37:
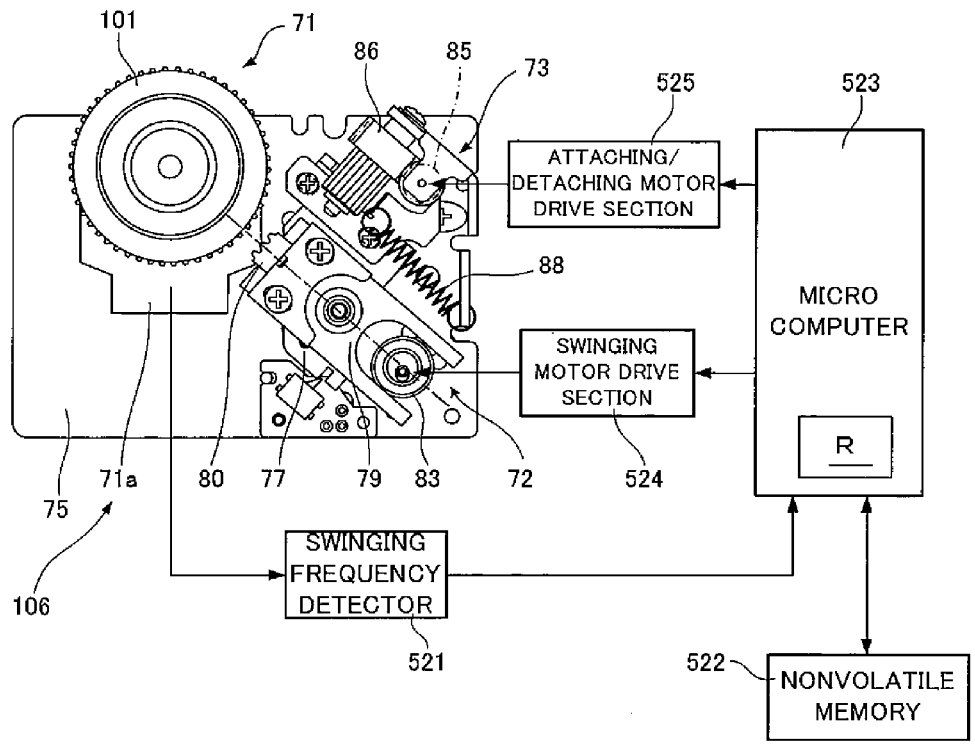
FIG. 37 is a structural diagram showing a rotational drive section according to the seventh embodiment.

In order to solve this problem, in the present invention, the swinging frequency of the first motor 71a during swinging is detected by a swinging frequency detector 521 as shown in FIG. 37, and a microcomputer 523 acting as a controller controls the second motor 72a so as to reduce Δf through a swinging motor drive section 524 based on the measured swinging frequency that has been read by the swinging frequency detector 521 and a table written in nonvolatile memory 522. In the present embodiment, the first motor 71a is made up of a brushless motor and contains a hole sensor for detecting the mechanical degrees of a rotor. Reciprocal motions made by agitation fluctuate the voltage of the detected output of the hole sensor. Thus the swinging frequency detector 521 detects the swinging frequency based on the voltage fluctuations of the detected output of the hole sensor. Further, the microcomputer 523 controls the timing of energization to the third motor 73a and the direction of rotation via an attaching/detaching motor drive section 525 during a swinging operation.

Immediately after the manufacturing of the analyzing apparatus 100, the microcomputer 523 is set at learn mode. In this learn mode, the measured value of the swinging frequency detector 521 is read while a set value outputted to the swinging motor drive section 524 is changed, and the microcomputer 523 writes the characteristic of the region a of FIG. 39 as a table in the nonvolatile memory 522.

Ideally in this learn mode, the swinging frequency is learned by measurement in a state in which the analyzing device 1 is set on the turntable 101. In the present embodiment, however, the swinging frequency is learned in a state in which the analyzing device 1 is not set on the turntable 101.

At the completion of learning, the microcomputer 523 is switched to analyzing operation mode.

The microcomputer 523 set at analyzing operation mode runs a swinging routine 400 of FIG. 40 in synchronization with the swinging of the analyzing process.

In step S1, the microcomputer 523 reads the table of a set value-swinging frequency relational expression written in the nonvolatile memory 522.

In step S2, the microcomputer 523 determines a set value necessary for obtaining a desired swinging frequency in the analyzing process, with reference to the table read in step S1. Further, the microcomputer 523 sets the set value for the swinging motor drive section 524.

In step S3, the third motor 73a is energized through the attaching/detaching motor drive section 525 to bring the second gear 80 close to the turntable 101, and the swinging driving motor drive section 524 is controlled to apply a direct-current voltage to the second motor 72a, the direct-current voltage having a voltage value corresponding to the set value. In step S4, the analyzing device 1 is swung.

In step S5, the microcomputer 523 having detected the passage of a specified swinging time completes the application of the direct-current voltage from the swinging driving motor drive section 524 to the second motor 72a, and energizes the third motor 73a through the attaching/detaching motor drive section 525 to separate the second gear 80 from the turntable 101, so that the current swinging operation is completed.

In step S6, a proper additional value is added to a register R based on the swinging frequency of the swinging operation at that time with reference to a part or the whole of an additional value table 126 shown in FIG. 41. The table 126 is determined beforehand by a friction experiment. To be specific, in the case where the register R has an accumulated value of N1 as a result of the previous swinging operation and the accumulated value is processed with reference to the top three lines of the additional value table 126, the accumulated value (accumulated swinging value) of the register R is increased by one and is updated to (N1+1) in step S6 at a swinging frequency of 10 Hz to 20 Hz determined at that time by the set value of step S2.

In the case of processing referring to the whole of the additional value table 126, the microcomputer 523 counts an elapsed time since the shipment of the analyzing apparatus from a factory or calculates an elapsed time from a difference between date data at different times and date data upon shipment from a factory. The microcomputer 523 updates the register R with reference to the top three lines of the additional value table 126 and adds an additional value according to the elapsed time. The additional value has a weight increasing with the elapsed time. To be specific, the accumulated value is increased by two between the third year and the fourth year of the elapsed time. Thus in this case, the accumulated swinging value is updated to (N1+1+2).

Figure 42:
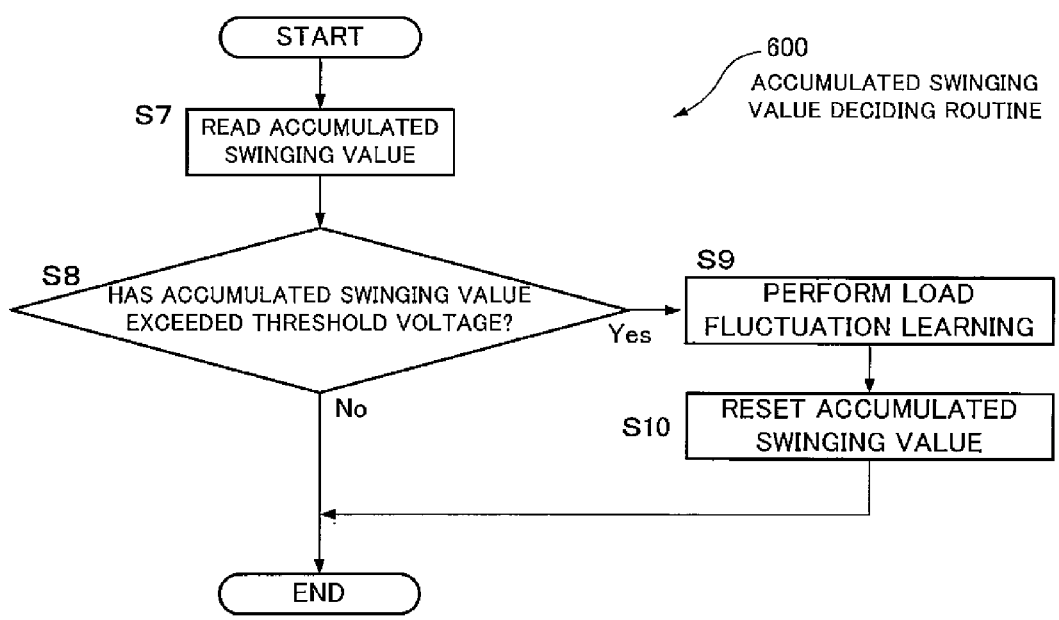
FIG. 42 is a flowchart showing an accumulated swinging value deciding routine according to the seventh embodiment.

At the completion of step S6 of the swinging routine 400, an accumulated swinging value deciding routine 600 of FIG. 42 is run at a proper time, for example, immediately after the end of the analyzing process.

In step S7, the microcomputer 523 reads the accumulated swinging value from the register R. In step S8, the microcomputer 523 checks whether the accumulated swinging value read in step S7 has exceeded a predetermined threshold value or not.

When it is decided in step S8 that the accumulated swinging value has not exceeded the threshold value, the accumulated swinging value deciding routine 600 is ended to return to the analyzing process.

When it is decided in step S8 that the accumulated swinging value has exceeded the threshold value, a load fluctuation learning routine 700 of step S9 is run. In the present embodiment, the load fluctuation learning routine 700 is run in a state in which the analyzing device 1 is not set on the turntable 101.

Figure 43:
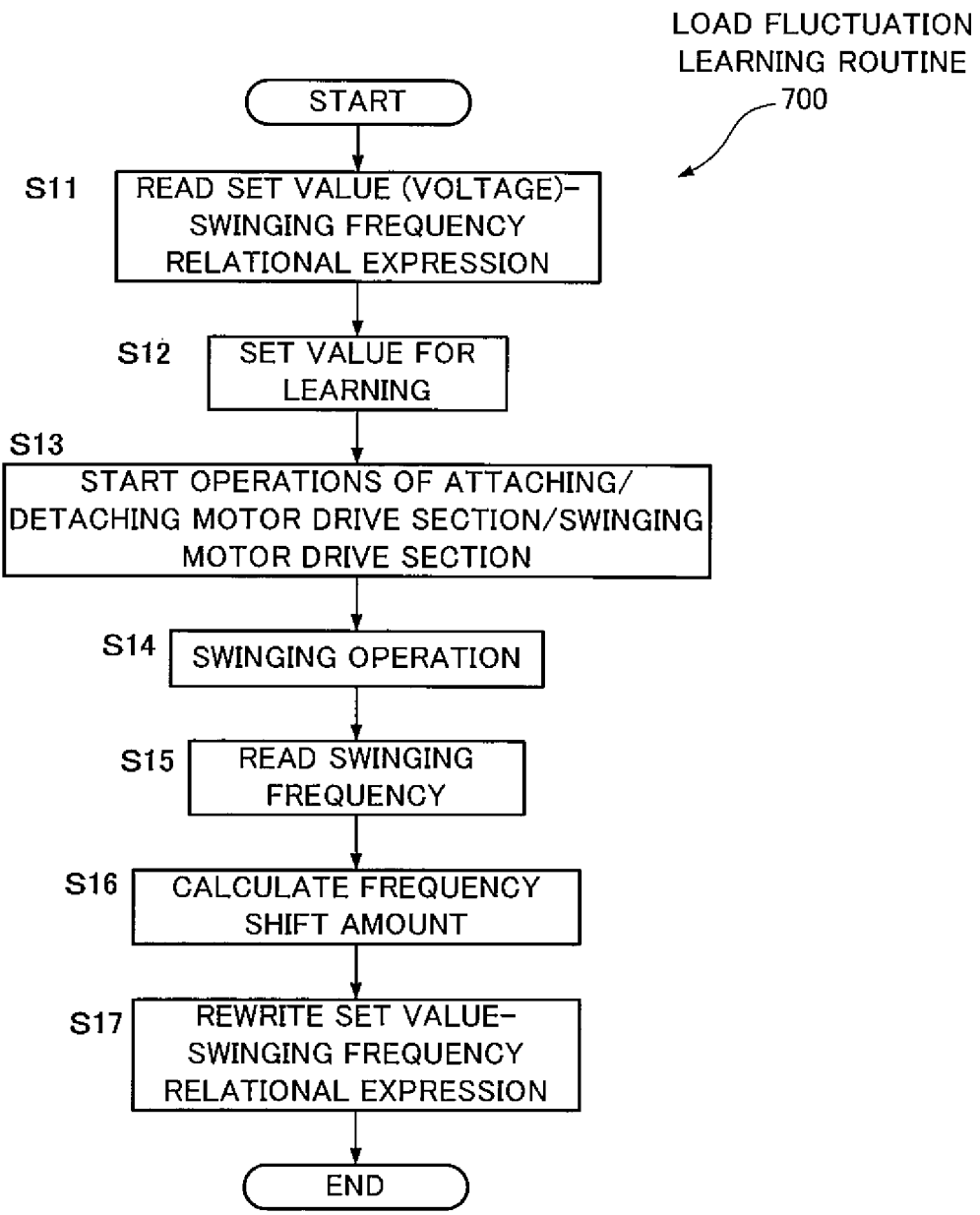
FIG. 43 is a flowchart showing a load fluctuation learning routine according to the seventh embodiment.

FIG. 43 shows the load fluctuation learning routine 700 of the microcomputer 523.

In step S11 of the load fluctuation learning routine 700, the table of the latest set value-swinging frequency relational expression written in step S1 is read from the nonvolatile memory 522.

In step S12, a predetermined set value for learning is read. In this case, the set value is 60.

In step S13, the third motor 73a is energized through the attaching/detaching motor drive section 525 to bring the second gear 80 close to the turntable 101, and the set value of 60, which has been read in step S12, is set for the swinging motor drive section 524. Thus swinging is performed in step S14. During the swinging, in step S15, the swinging frequency of the measured value outputted from the swinging frequency detector 521 is read. When the read value is β of FIG. 44, the shift amount of the swinging frequency is calculated in step S16 as follows:

$$\beta - \alpha = \Delta f$$

In step S17, the table of the nonvolatile memory 522 is updated such that Δf comes close to zero. To be specific, in FIG. 44, the point of the swinging frequency β measured at the set value of 60 is rewritten into a chain line table (after updating) on which the set value is vertically moved by ΔV so as to allow the passage of the current table (before updating) of the nonvolatile memory 522. At this moment, the set value for learning in the subsequent step S12 is updated to 50 that is necessary for obtaining the swinging frequency α in the updated table.

At the completion of step S17, the microcomputer 523 returns to the analyzing process after resetting the accumulated swinging value of the register R to zero in step S10 of FIG. 42, the accumulated swinging value having been written in step S6.

In this way, until the accumulated swinging value exceeds the threshold value in step S8 of FIG. 42, a set value necessary for a swinging operation at a specified swinging frequency is determined based on the latest table of the latest set value-swinging frequency relational expression read from the nonvolatile memory 522 every time swinging is designated in the analyzing process, and the swinging operation is performed in step S4. After that, the accumulated swinging value is updated in step S6. Thus the table of the nonvolatile memory 522 is updated by running the load fluctuation learning routine 700 of FIG. 43 at a proper time according to the contents of the swinging operation, so that even when the load of the second motor 72a fluctuates in the region a and the region b, it is possible to stabilize the swinging frequency during swinging, thereby eliminating variations in analysis.

The following will more specifically describe the stabilization of the swinging frequency during swinging.

In the case where the load fluctuation learning routine 700 of FIG. 43 is not run and the analyzing apparatus is operated over an extended period by using a set value upon shipment from a factory as a set value for instructing the swinging motor drive section 524, the instruction to the swinging motor drive section 524 is continued using the set value upon shipment from the factory as a set value regardless of the occurrence of deformation such as the wearing of a component. Thus even when the swinging operation is started at the set value and the swinging frequency is stabilized, the swinging frequency at this point is increased from a required swinging frequency by Δf because of the deformation such as the wearing of the component. Further, the swinging frequency is caused to reach the target swinging frequency during feedback control, so that a response time from the start of swinging to the arrival at the swinging frequency is increased and the contents of agitation are not stabilized in the response time.

Contrarily, in the present embodiment where the accumulated swinging value deciding routine 600 of FIG. 42 is run and the load fluctuation learning routine 700 of FIG. 43 is automatically run, a value learned to decrease Δf without reference to the table written in the nonvolatile memory 522 is used as a set value to instruct the swinging motor drive section 524. Thus Δf can be reduced as compared with the case where the set value upon shipment from a factory is used as a set value, and it is possible to shorten a response time when the swinging frequency is caused to reach the target swinging frequency during feedback control, thereby stabilizing the contents of agitation in the response time.

Figure 45:
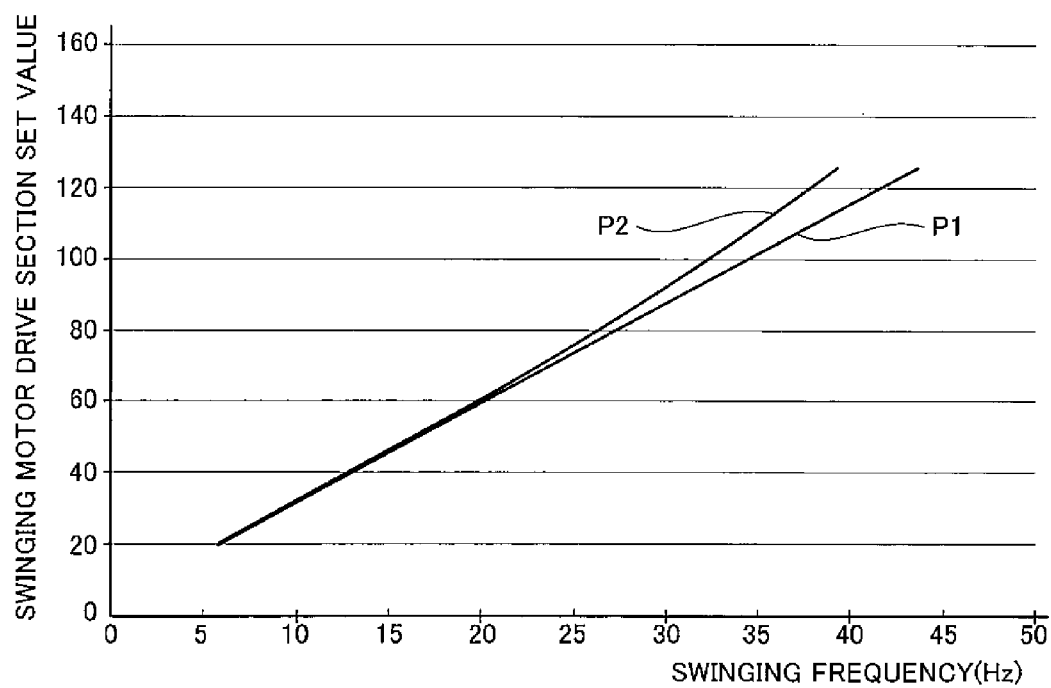
FIG. 45 shows the relationship between a set value and a swinging frequency with an analyzing device set on a turntable and the relationship between a set value and a swinging frequency with the analyzing device not set on the turntable.

In the present embodiment, swinging is performed in step S4 with reference to the table of the set value-swinging frequency relational expression learned in a state in which the analyzing device 1 is not set on the turntable 101. When the swinging frequency is measured while the set value is changed with the analyzing device 1 set on the turntable 101, a characteristic P2 in FIG. 45 and a characteristic P1 plotted when the analyzing device 1 is not set on the turntable 101 are substantially aligned with each other in a low-frequency swinging range of less than 25 Hz. In a high-frequency swinging range exceeding 25 Hz, however, a swinging frequency when the analyzing device 1 is set on the turntable 101 tends to be lower even at the same set value than in the case where the analyzing device 1 is not set on the turntable 101.

For this reason, when swinging is performed in the high-frequency swinging range, the characteristic P1 written in the nonvolatile memory 522 is multiplied by a specified coefficient for each swinging frequency to calculate the characteristic P2, the contents of the nonvolatile memory 522 are rewritten to the calculation result, and then step S4 is performed. Thus it is possible to swing the analyzing device 1 at a correct swinging frequency over a wide range from the low-frequency swinging range to the high-frequency swinging range.

Alternatively, without converting the characteristic P1 to the characteristic P2, the set value may be changed, the swinging frequency may be learned, the characteristic P2 may be written into the nonvolatile memory 522, and then step S4 may be performed in a state in which the analyzing device 1 is set on the turntable 101.

In the foregoing embodiments, the second drive part 72 is driven in engagement with the first gear 74 provided on the turntable 101. The first gear 74 may be formed on the outer periphery of the outer rotor 90 of the first motor 71a and the second gear 80 of the second drive part 72 may mesh with the first gear 74.

In the examples of the foregoing embodiments, the second gear 80 of the rotational drive section 106 gradually wears and the swinging frequency fluctuates. In the second embodiment of FIGS. 11 and 12, the rotational drive section 106 is configured such that the friction member 202 provided on one end of the lever 79 is brought into contact with the outer periphery of the turntable 101 to engage the turntable 101 with the lever 79. Also in this case, the friction member 202 may wear with the progress of an operation and cause an unstable swinging frequency, and Δf can be similarly controlled to decrease.

Eighth Embodiment

Figure 44:
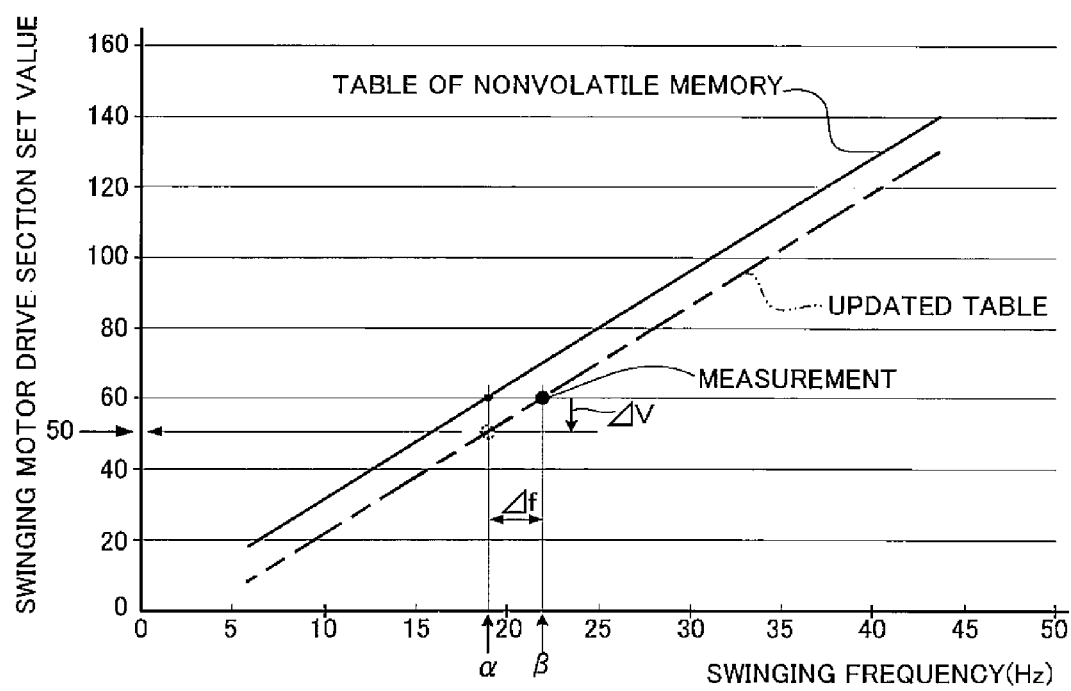
FIG. 44 is an explanatory drawing showing updating in the load fluctuation learning routine according to the seventh embodiment.

In the load fluctuation learning routine 700 according to the foregoing embodiments, the current solid-line table of the nonvolatile memory 522 in FIG. 44 is rewritten in steps S16 and S17 into the chain line table on which the set value is vertically moved by ΔV. By updating the contents of the nonvolatile memory 522 to results learned at multiple points as shown in FIGS. 46 to 48, more precise control can be achieved.

Figures 47, 48:
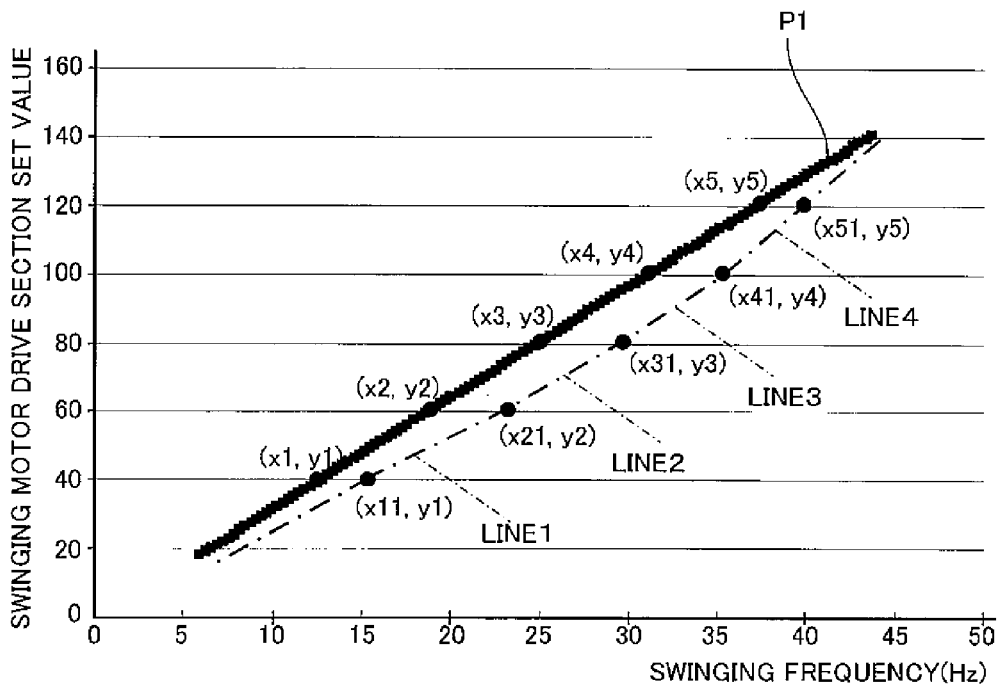
FIG. 47 is an explanatory drawing of FIG. 46.
FIG. 48 is an explanatory drawing showing a specific calculation example of FIG. 46.
Figure 49:
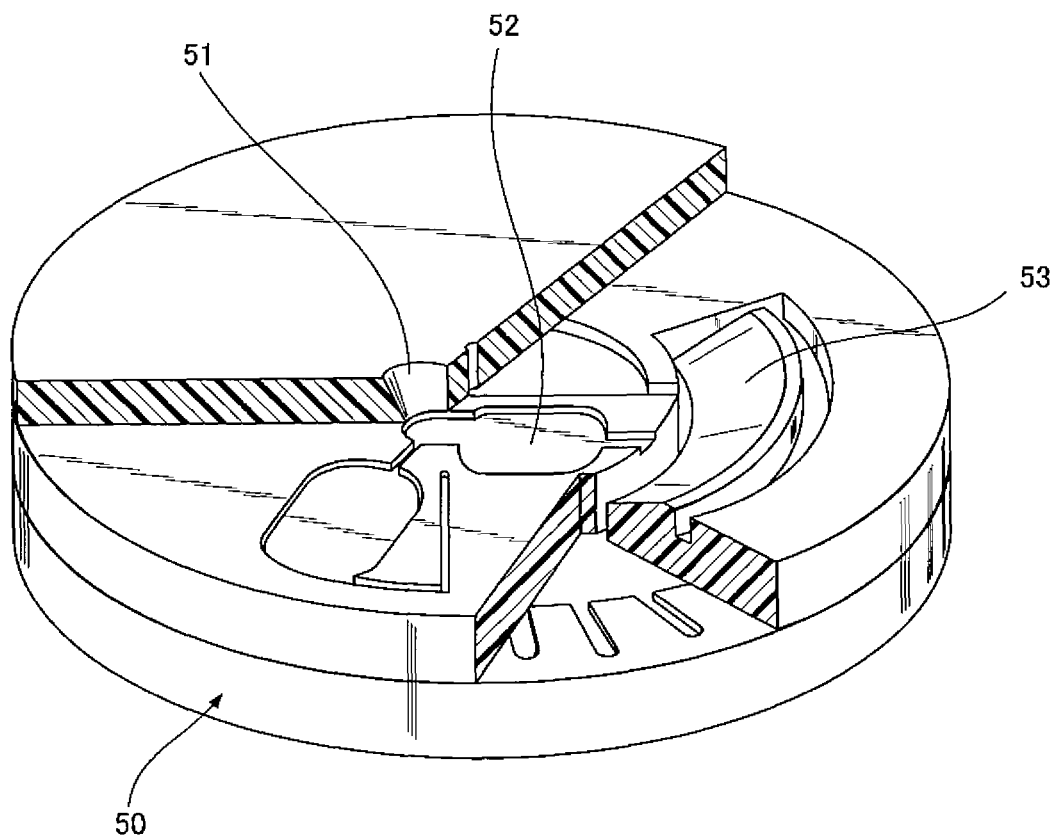
FIG. 49 is a partially cut perspective view showing an analyzing device of Patent Document 1.
Figure 50:
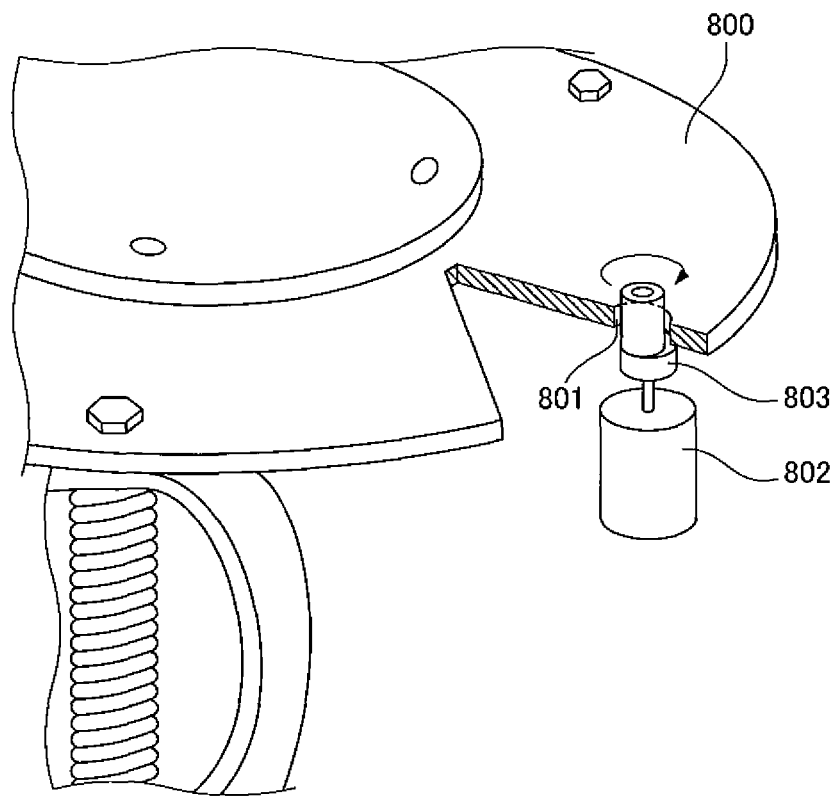
FIG. 50 is a partially cut perspective view showing Patent Document 2.

In the present embodiment, the current table of nonvolatile memory 522 has a characteristic P1 shown in FIG. 47. (x1, y1), (x2, y2), (x3, y3), (x4, y4), and (x5, y5) are the multiple points of the characteristic P1.

Figure 46:
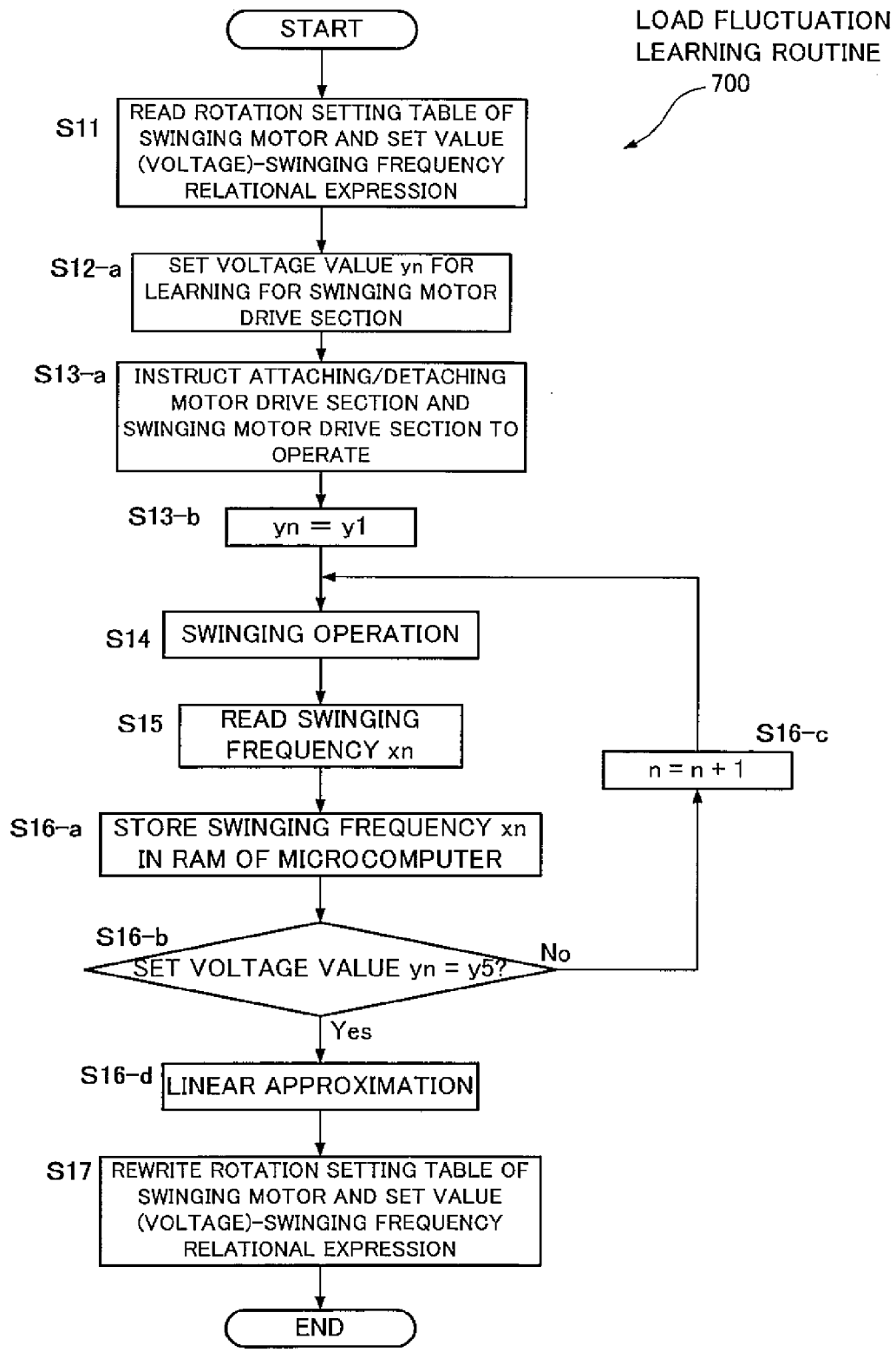
FIG. 46 shows the load fluctuation learning routine when swinging frequencies are measured and learned at multiple points.

In step S12-a of FIG. 46, the set values corresponding to the swinging frequencies at the multiple points (y1 to yn) are determined based on the table of the latest set value-swinging frequency relational expression. The table has been read from the nonvolatile memory 522 in step S11. In this case, the multiple points are five points of y1 to y5 and the set values of, for example, y1=40, y2=60, y3=80, y4=100, and y5=120 are set as shown in FIG. 47.

In step S13-a, a third motor 73a is energized through an attaching/detaching motor drive section 525 to bring a second gear 80 close to a turntable 101 and a swinging motor drive section 524 is instructed to operate.

In step S13b, the contents of a specific register in a microcomputer 523 are set at yn=y1. The register stores a measurement endpoint from the start of learning.

In step S14, a set value of 40 is set for the swinging motor drive section 524 based on y1 of the contents of the specific register and swinging is performed.

In step S15, a swinging frequency xn=x11 measured by the swinging frequency detector 521 at this moment is read.

In step S16-a, x11 read in step S15 is stored in RAM of the microcomputer 523 so as to correspond to the set value y1.

In step S16-b, it is decided whether or not the number of measured points is five, which is a specified value, after the completion of learning. In the case of yn≠y5, the contents of the specific register are updated to yn+1 in step S16-c and the process returns to step S14. Thus in the subsequent step S14, a set value of 60 is set for the swinging motor drive section 524 and swinging is performed. In step S15, a swinging frequency xn=x21 measured by the swinging frequency detector 521 is read. In step S16-a, x21 read in step S15 is stored in the RAM of the microcomputer 523 so as to correspond to the set value y2.

Until yn=y5 is detected in step S16-b, a routine of step S16-c to step S16-a is repeated to learn (x11, y1), (x21, y2), (x31, y3), (x41, y4), and (x51, y5).

In step S16-d, a line 1 between (x11, y1) and (x21, y2) undergoes linear approximation, a line 2 between (x21, y2) and (x31, y3) undergoes linear approximation, a line 3 between (x31, y3) and (x41, y4) undergoes linear approximation, and a line 4 between (x41, y4) and (x51, y5) undergoes linear approximation. The contents of the nonvolatile memory 522 are updated to a table containing the line 1, the line 2, the line 3, the line 4, a line located under (x11, y1) and designated as the line 1, and a line located above (x51, y5) and designated as the line 4. FIG. 48 shows a specific example of the calculation of the lines 1 to 4.

In the foregoing embodiments, the nonvolatile memory 522 is updated in a state in which the analyzing device 1 is not set upon shipment from a factory and the subsequent learning. Thus the nonvolatile memory 522 can be updated to an optimum value in a standby time until power is supplied to the analyzing apparatus and the analyzing device 1 is set. As previously mentioned, the nonvolatile memory 522 can be updated in a state in which the analyzing device 1 is set upon shipment from a factory and the subsequent learning.

INDUSTRIAL APPLICABILITY

According to the present invention, the mixing and agitation of an analyzing device used for analyzing a component of a liquid collected from an organism and the like can be performed in a short time. Further, it is possible to keep analysis accuracy and improve analysis efficiency.

The invention claimed is:

1. A driving apparatus for an analyzing apparatus comprising a rotational drive section having a first drive part for rotating a set analyzing device, a second drive part selectively engaged with the first drive part to reciprocate the analyzing device, and a third drive part for relatively moving the first drive part and the second drive part to a position where the first and second drive parts are engaged with each other and a position where the first and second drive parts are not engaged with each other, the driving apparatus further comprising:
a swinging frequency detector configured to detect a swinging frequency of the first drive part;
a controller configured to output a set voltage value to the second drive part, the set voltage value being necessary for swinging the analyzing device; and
memory configured to store a table that expresses a relationship between the set voltage value and the swinging frequency,
wherein the controller is configured to run a learning routine, the learning routine comprising:
reading the table stored in the memory;
outputting a set voltage value to the second drive part;
reading a detected value of the swinging frequency that is detected by the swinging frequency detector, and
updating the table so as to reduce difference between the detected value and a corresponding value of the swinging frequency that corresponds to the set voltage value in the table before updated,
wherein the updating process in the learning routine includes:
determining a shift amount of swinging frequency based on a difference between the detected value and the corresponding value of the swinging frequency;
calculating a voltage adjustment based on the set voltage value, the shift amount of swing frequency and a relationship between the set voltage value and the corresponding value of the swinging frequency in the table; and
rewriting the set voltage value in the table based on the voltage adjustment such that a further detected value corresponding to the updated set voltage value comes closer to the corresponding value of the swing frequency.

2. The driving apparatus for the analyzing apparatus according to claim 1, wherein the controller is configured to run an accumulated swinging value deciding routine, the accumulated swinging value deciding routine comprising:
accumulating count values corresponding to contents of a swinging operation to an accumulated value in a resister;
running the learning routine when the controller detects that the accumulated value has exceeded a threshold value; and
resetting the accumulated value when the learning routine has been completed.

3. The driving apparatus for the analyzing apparatus according to claim 1, wherein the controller is configured to run an accumulated swinging value deciding routine, the accumulated swinging value deciding routine comprising:
accumulating count values corresponding to contents of a swinging operation and the secular changes to an accumulated value in a resister,
running the learning routine when the controller detects that the accumulated value has exceeded a threshold value; and
resetting the accumulated value when the learning routine has been completed.

4. The driving apparatus for the analyzing apparatus according to claim 1, wherein the first drive part contains a hole sensor, and the swinging frequency detector is configured to detect the swinging frequency of the first drive part based on voltage fluctuations of a detected output of the hole sensor.

\* \* \* \* \*